(12) United States Patent
Shah

(10) Patent No.: US 10,638,999 B2
(45) Date of Patent: May 5, 2020

(54) SYSTEM FOR CONTROLLING MEDICAL DEVICES

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 693 days.

(21) Appl. No.: 15/430,461

(22) Filed: Feb. 11, 2017

(65) Prior Publication Data

US 2017/0150939 A1 Jun. 1, 2017

Related U.S. Application Data

(63) Continuation-in-part of application No. 13/756,445, filed on Jan. 31, 2013, now abandoned.
(Continued)

(51) Int. Cl.
| | |
|---|---|
| A61B 6/00 | (2006.01) |
| H04L 5/14 | (2006.01) |
| A61B 5/07 | (2006.01) |
| A61B 5/00 | (2006.01) |
| A61M 16/00 | (2006.01) |

(Continued)

(52) U.S. Cl.
CPC ............ *A61B 6/548* (2013.01); *A61B 5/076* (2013.01); *A61B 5/6861* (2013.01); *A61M 16/0069* (2014.02); *A61M 16/0447* (2014.02); *A61M 16/1005* (2014.02); *A61M 16/202* (2014.02); *G01S 19/14* (2013.01); *G16H 10/60* (2018.01); *G16H 40/63* (2018.01); *G16H 40/67* (2018.01); *H04L 5/14* (2013.01); *H04L 67/02* (2013.01); *H04L 67/025* (2013.01); *H04L 67/12* (2013.01); *A61B 6/4464* (2013.01); *A61B 6/54* (2013.01); *A61B 6/541* (2013.01); *A61B 6/542* (2013.01); *A61B 6/563* (2013.01); *A61B 6/566* (2013.01); *A61B 6/586* (2013.01);
(Continued)

(58) Field of Classification Search
None
See application file for complete search history.

(56) References Cited

U.S. PATENT DOCUMENTS

| | | | |
|---|---|---|---|
| 3,604,860 A | 9/1971 | Buchheit | |
| 2004/0030235 A1* | 2/2004 | Sasaki | A61B 6/541 600/413 |

(Continued)

*Primary Examiner* — Devin C Hein
(74) *Attorney, Agent, or Firm* — Rahman LLC

(57) ABSTRACT

Controlling a multi-device module includes a physiological sensor configured to sense physiological characteristics of a subject and generate a signal indicative of an instantaneous physiological state. A first device is configured to generate a first signal indicative of an operating state of the first device. A second device is configured to generate a second signal indicative of an operating state of the second device. A remote-control device includes a repository for storing computer executable files aggregated from a plurality of changing private networks. The remote-control device includes an electronic record (ER) client to make a wireless connection with each of the private networks and to query ER database associated with the private networks for electronic records residing within the private networks.

20 Claims, 13 Drawing Sheets

Related U.S. Application Data

(60) Provisional application No. 61/594,224, filed on Feb. 2, 2012.

(51) Int. Cl.
| | |
|---|---|
| *A61M 16/10* | (2006.01) |
| *A61M 16/04* | (2006.01) |
| *A61M 16/20* | (2006.01) |
| *H04L 29/08* | (2006.01) |
| *G16H 10/60* | (2018.01) |
| *G16H 40/67* | (2018.01) |
| *G16H 40/63* | (2018.01) |
| *H04L 29/06* | (2006.01) |
| *G01S 19/14* | (2010.01) |

(52) U.S. Cl.
CPC ............ *A61M 2202/0208* (2013.01); *A61M 2205/3592* (2013.01); *H04L 67/42* (2013.01)

(56) References Cited

U.S. PATENT DOCUMENTS

| | | |
|---|---|---|
| 2004/0082853 A1 | 4/2004 | Sasaki et al. |
| 2007/0005397 A1 | 1/2007 | Lee |
| 2007/0185389 A1 | 8/2007 | Peng |
| 2008/0312961 A1 | 12/2008 | Alsafadi |
| 2009/0036750 A1 | 2/2009 | Weinstein et al. |
| 2009/0319298 A1 | 12/2009 | Weiss et al. |
| 2010/0324936 A1 | 12/2010 | Vishnubhatla et al. |
| 2013/0110528 A1 | 5/2013 | Steinhauer et al. |
| 2013/0338450 A1 | 12/2013 | Osorio et al. |

\* cited by examiner

FIG. 8

| DEVICE | OPERATING STATE | INTERDEPENDENCE | OPERATING STATE |
|---|---|---|---|
| D1 | PERFORMING | D2, D3, D6 | NON-PERFORMING |
| D2 | PERFORMING | D1, D3, D8 | NON-PERFORMING |
| D3 | PERFORMING | D1, D2, D9 | NON-PERFORMING |
| D4 | PERFORMING | D10, D12 | NON-PERFORMING |
| D4 | PERFORMING | D13, D16 | UNINFLUENCED |
| D2 | PERFORMING | D4 | PERFORMING |

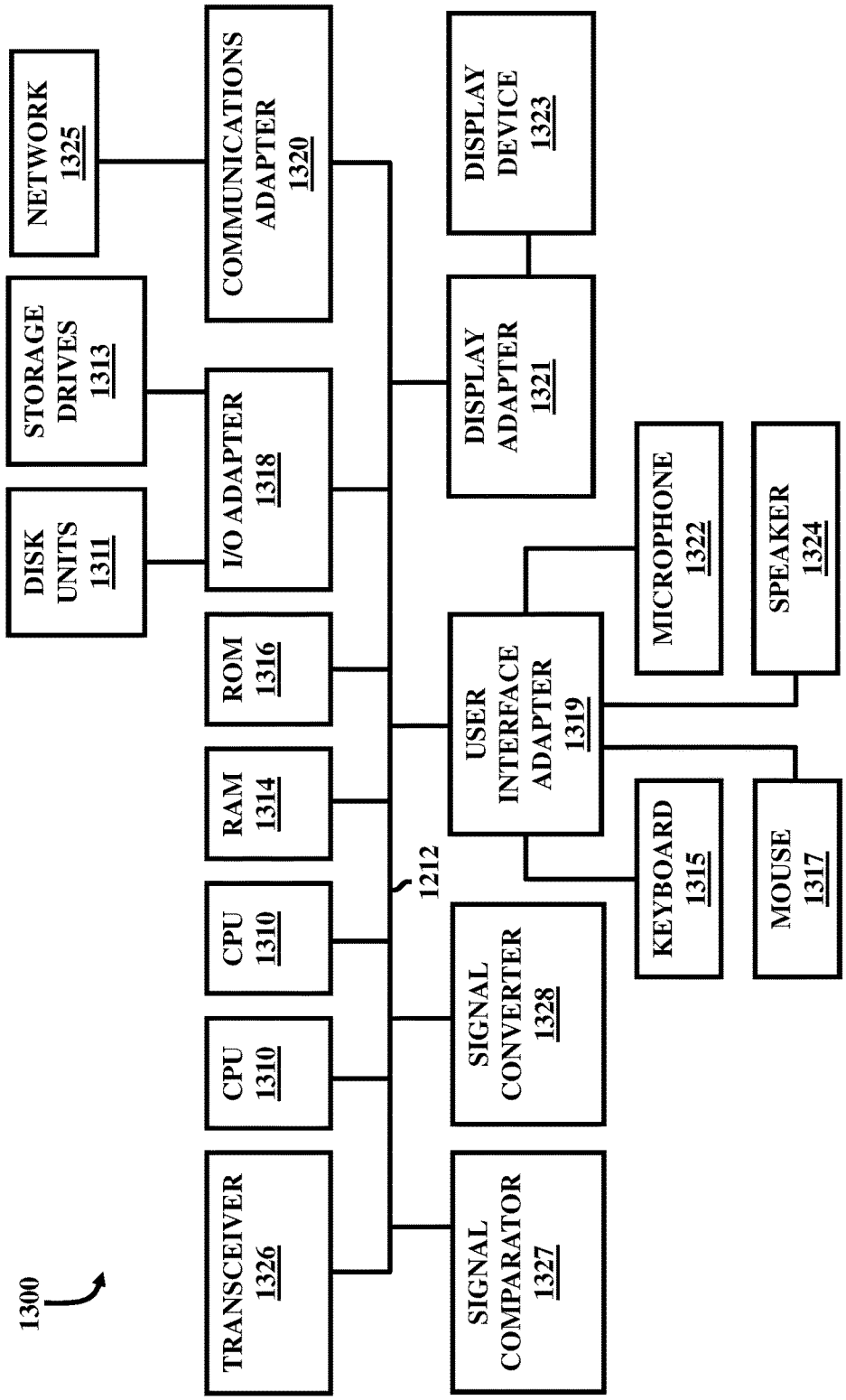

SYSTEM FOR CONTROLLING MEDICAL DEVICES

CROSS-REFERENCE TO RELATED APPLICATIONS

This application is a continuation-in-part of U.S. patent application Ser. No. 13/756,445 filed on Jan. 31, 2013, which claims priority to U.S. provisional application No. 61/594,224, filed on Feb. 2, 2012, the complete disclosures of which, in their entireties, are hereby incorporated by reference.

BACKGROUND

Technical Field

The embodiments herein generally relate to medical devices, and more particularly, to systems for controlling medical devices.

Description of the Related Art

Hospitals, caretakers, nursing centers or homes, medical offices, medical centers, or other sources of medical care and entities generally keep medical and demographic or other such records of their patients. These records may include a variety of information such as demographic information of their patients, medical history, diagnostic and pathology reports of their patients, medical reports or prescriptions, or other such information. This information can be used for a variety of purposes by these sources of medical care. A few examples of them are, without limitations, tracking of the patients and their records, billing, historical assessments, integrating with medical devices, remote care, future care taking, telemedicine, proper ongoing medical or health assessment or treatment, or any other purpose.

One way to collate and store the medical data is with the use of an electronic health record data bank (EHRDB). These records from various entities can be electronically maintained such as by the electronic health record data bank (EHRDB) in a central system accessible by the entities. The EHRDB may store medical data of the entities and devices and retrieve the data of the respective entities as and when requested by them.

SUMMARY

An embodiment herein provides a system for controlling multiple devices, the system comprising a physiological sensor associated with a body of a subject and configured to sense one or more physiological characteristics of the subject and generate a digital physiological signal indicative of an instantaneous physiological state of the subject; a first device configured for bi-directional wireless communication positioned proximate to the subject and comprising a first memory circuit and a first processor, wherein the first device is configured to generate a first signal indicative of an operating state of the first device, and wherein the operating state comprising one of a performing state and a non-performing state of the first device; a second device configured for bi-directional wireless communication positioned proximate to the subject and comprising a second memory circuit and a second processor, wherein the second device is configured to generate a second signal indicative of an operating state of the second device, wherein the operating state comprising one of a performing state and a non-performing state of the second device, and wherein the first device and the second device are configured to perform one of a therapeutic, diagnostic, and a medication delivery task on the subject in accordance with computer-enabled instructions; a computer with telemetry circuitry for communicating with the physiological sensor, the first device, and the second device; and a remote-control device positioned apart from the physiological sensor, the first device, and the second device.

The remote-control device comprises a digital records repository comprising a memory circuit and a processing unit for storing dynamically updating computer executable files aggregated from a plurality of changing private networks wherein the computer executable files contain dynamically updating digitally recorded information indicative of a set of changing subject attributes and respective changing reference values associated with the subject; an electronic record (ER) client configured to make a wireless connection with each of the private networks and configured to query an ER database associated with each of the private networks for electronic records residing within the private networks; a server machine configured for communicating with the physiological sensor, the first device, and the second device either directly or through the computer, wherein the server machine is configured for receiving the digital physiological signal indicative of the instantaneous physiological state of the subject and sending programmable operational parameters to the first device and the second device in response to a request for service from the computer and based on the instantaneous physiological state such that the operating parameters decides operating characteristics of the first device and operating characteristics of the second device and the operating characteristics of the first device and the operating characteristics of the second device are interdependent through a priority and interdependence relationship, wherein at least one of the physiological sensor, the first device, the second device, and the computer transforms the received operating parameters into a digital data structure readable by a scanner; and an identity validation device to verify an identity of the first device and the second device and associate a subject identifier uniquely representing the subject with the first device and the second device based on information contained within the physiological signal such that the operating parameters are calculated based on one or more of the reference values associated with the subject having the unique subject identifier as identified based on the physiological signal.

The physiological sensor may be implanted within the body of the subject subcutaneously. The physiological sensor may be associated with the subject as an external device. The physiological sensor may be configured for the subject such that the digital physiological signal contains the subject identifier along with an information indicative of the instantaneous physiological state of the subject. The remote-control device may be configured to associate the subject identifier with the computer executable files stored in the digital records repository to retrieve the reference values associated with the subject and generate an output indicative of the operational parameters of the first device and the second device based on the physiological signal and the retrieved reference values associated with the subject. The operational parameters may comprise any of changing an operating state of the first device only for a first period of time; changing an operating state of the second device only for a second period of time; changing an operating state of both the first device and the second device for a third period of time; and connecting a third device different from the first device and the second device by associating an operating state with the third device in association with the subject for a fourth period of time, wherein each of the first device, the second device, and the third device are uniquely identified by device identifiers such that the digital records repository stores the digital identifiers in a device manager in association with the subject identifier.

Any of the server machine and the computer may further comprise a switch matrix configured to cause switching of the operating state of the one or more of the first device, second device, and the third device upon receipt of the operational parameters from the remote-control device in accordance with the priority and interdependence relationships. The remote-control device may further comprise a time detection circuit configured to monitor the first period of time, second period of time, third period of time, and the fourth period of time. The system may further comprise a device state detection circuit coupled to the time detection circuit and configured to identify an operating state of the first device, second device, and the third device after completion of the first period of time, the second period of time, the third period of time, and the fourth period of time. The system may further comprise a fault detection circuit configured to generate a signal indicative of a fault when the device state detection circuit does not detect a change in operating states of either of the first device, second device, or the third device in accordance with the operational parameters transmitted by the remote-control device. The first device may comprise a ventilator and the second device may comprise an X-ray machine such that the remote-control device causes the ventilator to perform a first action upon receipt and the X-ray machine to perform a second action upon receipt of the operational parameters.

The remote-control device may comprise an electronic medical record (EMR) system configured to house a plurality of digital records associated with a plurality of subjects including the subject in the form of a plurality of digital files including the computer executable files associated with the subject, wherein the EMR system comprising the digital records repository; the electronic record (ER) client; a mobile point of care system to capture subject-associated digital data at a point of care wherein the point of care system is communicatively connected with the electronic record (ER) client so as to transmit the electronic records captured by the mobile point of care system from the private networks to the server machine; a data interface, in communication with the mobile point of care system, to facilitate transmission of the electronic records to the server machine; and a web-based interactive graphical user interface for allowing the subject to enter the digital records manually from a distant location. The digital data structure may comprise a QR (quick response) code.

Another embodiment provides a multi-device system comprising a first medical device configured for bi-directional wireless communication positioned proximate to a subject and comprising a first memory circuit and a first processor, wherein the first medical device is configured to generate a first signal indicative of an operating state of the first medical device, and wherein the operating state comprising one of a performing state and a non-performing state of the first medical device; and a second medical device configured for bi-directional wireless communication positioned proximate to the subject and comprising a second memory circuit and a second processor, wherein the second medical device is configured to generate a second signal indicative of an operating state of the second medical device, and wherein the operating state comprising one of a performing state and a non-performing state of the second medical device.

Each of the first medical device and the second medical device comprise an integrated gateway device configured to have a multiple interface unit comprising data interface units configured to send medical operation measurements in conformity with one or more operational parameters received via any of a wired and wireless communication network; a medical device housing to contain device accessories and circuitry; one or more of a therapeutic delivery device, a medication delivery device, and a diagnosis device physically contained within the medical device housing and configured to perform one of a therapeutic, diagnostic, and a medication delivery task; an identification module to contain digitally stored information indicative of device identifier and configured to be transmitted to other devices upon request for device identification; and a computer with telemetry circuitry for communicating with a physiological sensor, the first device, and the second device, wherein the computer is configured to receive a physiological signal from the associated physiological sensor configured for a subject; transmit a subject identifier, a first medical device identifier associated with the first medical device, and a second medical device identifier associated with the second medical device along with a service request to a remote-control device positioned apart from the physiological sensor, and wherein the remote-control device is configured to fulfill the service request based on information contained in a plurality of dynamically updating computer executable files from a plurality of digital data sources and stored in an EMR system configured within the remote-control device; and receive the one or more operational parameters from the remote-control device in response to a service request from the computer and based on an instantaneous physiological state as identified from the physiological signal such that the one or more operating parameters decides operating characteristics of the first medical device and operating characteristics of the second medical device, wherein the operating characteristics of the first medical device and the operating characteristics of the second medical device are interdependent through a priority and interdependence relationship.

The first medical device may comprise a medical imaging machine for imaging of a target including a tissue or a bone structure within a body of a subject, the medical imaging machine comprising a rotatable drive shaft; an imaging device supported on the rotatable drive shaft, the imaging device adapted to transmit energy toward the target; a position adjustment mechanism coupling with the rotatable shaft to allow adjustment of the rotatable drive shaft in order to focus transmission of the energy at the target; the integrated gateway device; and the identification module. The energy may comprise X-rays and the imaging machine may comprise an X-Ray machine.

The second medical device may comprise a life support system comprising an oxygen source that includes a tank of pressurized gas; one or more control valves disposed over a channel connecting the oxygen source and the subject to allow the oxygen to flow from the tank to a laryngeal mask in a first state and to allow gas expelled from the subject to flow from the laryngeal mask to the atmosphere in a second state while preventing the oxygen from flowing from the oxygen source in a second state; the laryngeal mask disposed downstream from the inspiration control valve, the laryngeal mask configured to form an air seal with the subject's respiratory tract such that the oxygen flows from the oxygen source to the lungs of the subject; a timer for synchronizing actuation of the one or more control valves based on the operational parameters received from the remote-control device containing the EMR system; the integrated gateway device; and the identification module. The life support system may comprise a ventilator. Each of the first medical device and the second medical device may comprise a respective (Global Positioning System) GPS-based device such that the GPS-based device is configured to detect geo-locations of the respective first medical device and the second medical device, wherein the remote-control device receives the detected geo-locations of the first medical device and the second medical device, and the remote-control device automatically correlates the subject identifier for the subject associated with the first medical device and the second medical device and initiates functioning in context of the subject as and when the EMR system is proximate to the subject associated with the first medical device and the second medical device. The computer may be configured to transform the operating parameters received from the remote-control device into a digital data structure, the system further comprising a scanner communicatively coupled to the computer such that the digital data structure is readable by the scanner.

BRIEF DESCRIPTION OF THE DRAWINGS

The features of the disclosed embodiments may become apparent from the following detailed description taken in conjunction with the accompanying drawings showing illustrative embodiments herein, in which:

FIG. 8 illustrates an exemplary lookup table depicting interdependence among a plurality of medical devices, in accordance with an embodiment;

FIG. 13 illustrates generally, but not by the way of limitation, a computer system that may be used in accordance with the embodiments herein.

DETAILED DESCRIPTION

Figure 1:
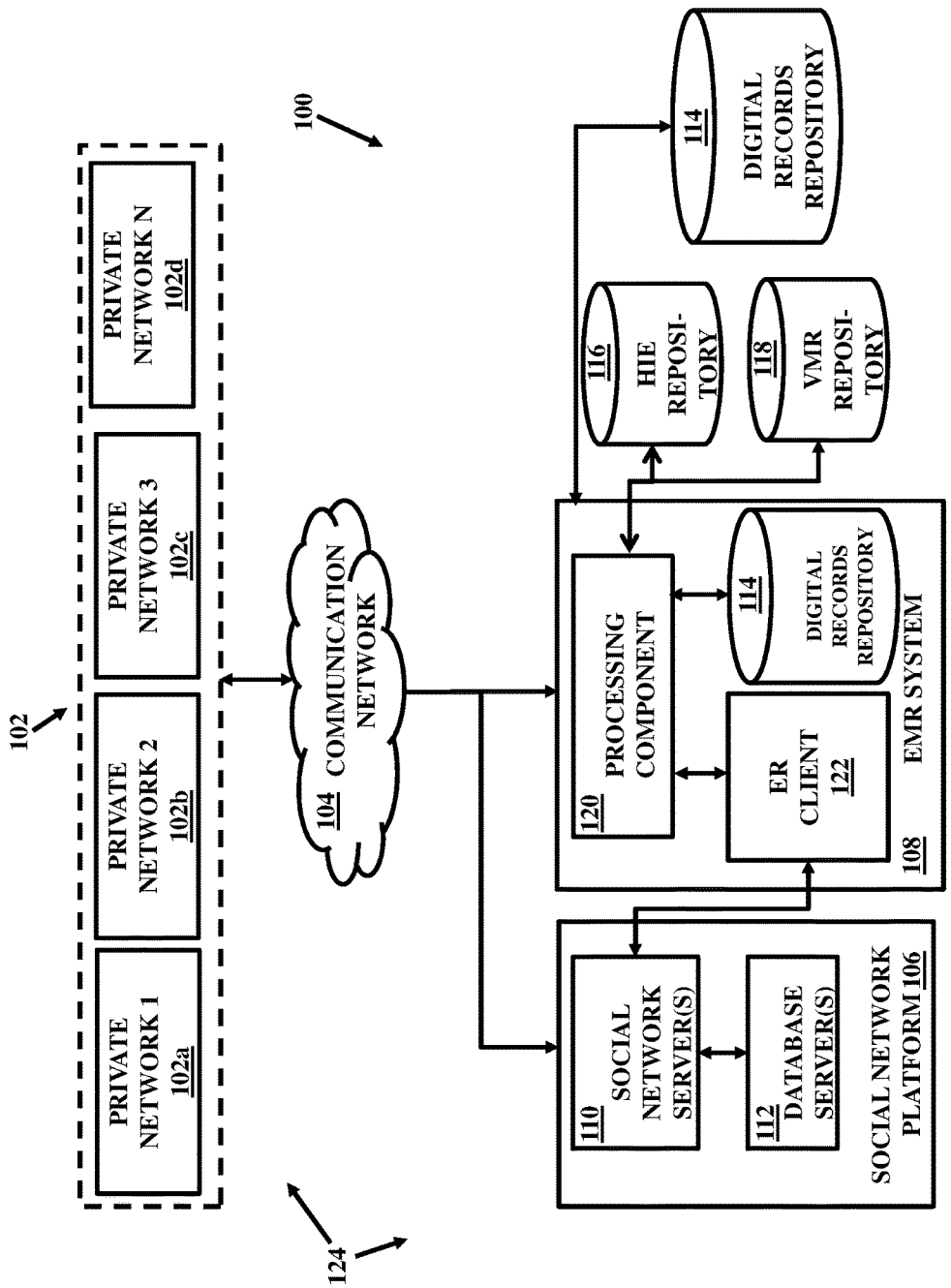
FIG. 1 illustrates generally, but not by the way of limitation, among other things, an example of an operating environment in which an embodiment may operate.

The embodiments herein and the various features and advantageous details thereof are explained more fully with reference to the non-limiting embodiments that are illustrated in the accompanying drawings and detailed in the following description. Descriptions of well-known components and are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In the following detailed description, reference is made to the accompanying drawings that form a part hereof, and these are shown by way of illustrating specific embodiments herein that may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

In this document, the terms "a" or "an" are used, as is common in patent documents, to include one or more than one. In this document, the term "or" is used to refer to a "nonexclusive or" unless otherwise indicated.

In an exemplary embodiment, the various modules described herein and illustrated in the figures are embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that are configured with electronic circuits process computer logic instructions capable of providing digital and/or analog signals for performing various functions as described herein. The various functions can further be embodied and physically saved as any of data structures, data paths, data objects, data object models, object files, database components. For example, the data objects could be configured as a digital packet of structured data. The data structures could be configured as any of an array, tuple, map, union., variant, set, graph, tree, node, and an object, which may be stored and retrieved by computer memory and may be managed by processors, compilers, and other computer hardware components. The data paths can be configured as part of a computer CPU that performs operations and calculations as instructed by the computer logic instructions. The data paths could include digital. electronic circuits, multipliers, registers, and buses capable of performing data processing operations and arithmetic; operations (e.g., Add, Subtract, etc.), bit se logical operations (AND, OR, XOR, etc.), bit shift operations arithmetic, logical, rotate, etc.), complex operations (e.g., using single clock calculations, sequential calculations, iterative calculations, etc.). The data objects may be configured as physical locations in computer memory and can be a. variable, a data structure, or a function. In the embodiments configured as relational databases (e.g., such Oracle® relational databases), the data objects can be configured as a table or column. Other configurations include specialized objects, distributed objects, object oriented programming objects, and semantic web objects, for example. The data object models can be configured as an application programming interface for creating HyperText Markup Language (HTML) and Extensible Markup Language (XML) electronic documents. The models can be further configured as any of a tree, graph, container, list, map, queue, set, stack, and variations thereof. The data object files are created by compilers and assemblers and contain generated binary code and data for a source file. The database components can include any of tables, indexes, views, stored procedures, and triggers.

A method or a system for dynamically updating real-time digital data associated with one or more entities of an electronic medical record (EMR) system is provided herein. The system and method comprises an ER client to remotely collect the real-time digital data associated with the one or more entities over a communication network.

The real-time digital data may include, for example data related to patient, clinician, labs and imaging center, clinical research center, healthcare financing institute, pharmacy, nursing, social services, clinical or medical devices and the like. The ER client analyses the collected digital data to update one or more repositories of the EMR system associated with the one or more entities in real-time. The EMR system may also run automated monitoring software to alert the one or more entities about the updated digital records and associated digital data.

FIG. 1 illustrates generally, but not by the way of limitation, among other things, an exemplary operating environment 100 in which various embodiments may operate. The environment 100 provides a high-level view of one or more private networks 102 serving as digital data sources for the Electronic Medical Record (EMR) system 108 such that the digital data may be accessed by the EMR system 108 in real time over a communications network 104. These private networks 102 may be associated with a plurality of entities such that the entities can be various subjects (patients), healthcare providers, care takers, and the like. Each private network 102 is associated with a particular subject such that the digital data available in a particular private network 102 is accessible to only the subject and his care takers or care providers or any other entity allowed by the subject or his care taker or his care provider to access the private network 102. In accordance with the digital data associated with the subject, the EMR system 108 may also reserve rights such that the digital data accessed from the private network 102 of the subject is accessible according to privacy and ownership rights of the digital data by the subject. The private networks may be associated with local private digital databases wherein the digital data associated with the subjects may be stored. The private networks may also refer to manual entries of the digital data at least in part by the subjects or associated entities. The private networks may also refer to automated or manual pulling of the digital data from associated medical devices of the subjects.

In an embodiment, the EMR system 108 may be coupled to social networks such as through the social network platform 106 which may also serve as a source of the digital data associated with the subjects. In an embodiment, the social networking platform 106 may generate a variety of data coming from various aggregators and user profiles comprising of a plurality of digital formats wherein each digital format may be associated with a specific structure different from other digital formats. The data originating from the social networking platform 106 may require complex mapping of fields and elements for transformation to a unified structure as per requirements. The social networking platform 106 may host information related to the subjects. For example, the social networking platform 106 may host social profiles of the subjects and/or related entities such as caretakers where they may store and update their personal, professional or other such details or may communicate in a social network with friends, relatives, family members, or other such networking contacts about healthcare information or patient or medical device generated information, in an example. The social networking platform 106 may be defined as a network with an arbitrary large number of networked computers accessing the social network 106 through registered social profiles of such as clinical data providers or subjects. The social networking platform 106 may facilitate posting and sharing online profiles, data, clinical reviews, patient generated data, device generated data, IoT data, sensors data etc., simultaneously viewable by each of the arbitrary large number of computers including such as a clinical provider computer, patient computer, and the like.

The communication network 104 can provide a communicative interconnection of various nodes such as the private networks 102, social network platform 106, EMR system 108, or any other node in the communication network 104. The private networks 102 and the social network platform 106 are together referred to as digital data sources 124 associated with a subject. The digital data sources 124 may be connected with their respective computing devices. The communication network 104 may include one or more wireless communications network or one or more wire line communications network.

The wireless communications network may include for example, but not limited to, a digital cellular network, such as Global System for Mobile Telecommunications (GSM) network, Personal Communication System (PCS) network, or any other wireless communications network. The wire line communications network may include for example, but not limited to, a Public Switched Telephone Network (PSTN), proprietary local and long distance communications network, or any other wire line communications network. In addition, the communication network 104 may include for example, digital data networks, such as one or more local area networks (LANS), one or more wide area networks (WANS), or both LANS and WANS to allow interaction among the digital data sources and the EMR system. One or more networks may be included in the communication network 104 and may include both public networks such as the Internet, and private networks and may utilize any networking technology and protocol, such as Ethernet, Token Ring, Transmission Control Protocol/Internet Protocol (TCP/IP), or the like to allow interaction among various nodes such as the digital data sources, and the EMR system 108, or any other node in the network 104.

The digital data sources 124 described herein may be connected with, for example, any type of electronic data processing system or communication device connected to the communications network 104. Examples of such an electronic data processing system include personal computer systems, such as desktop or laptop computers, workstation computer systems, server computer systems, networks of computer systems, personal digital assistants (PDAs), wireless communications devices, portable devices, or any other electronic data processing system. Likewise, the digital data sources 124 can connect to the communication network 104 through a wired or wireless connection, or a combination thereof, directly or indirectly. An "entity" is understood to mean an individual or a group of individual or an organization, or a platform such as for whom digital data is managed or who manages the digital data or who facilitate managing of the digital data in the EMR system 108. The entities may include for example, but not limited to a subject/patient, clinician or doctor, a lab and research organization, a biller, a hospital, an insurance corporation, an emergency resource such as ambulance, a marketer, an advertiser, an enterprise, a sponsor, an office professional, a social service organization, or any other individual or a group of individuals or an organization or a platform. Each subject can be associated with a unique subject identifier, usually comprising of a numeric or alphanumeric sequence that is unidentifiable outside the EMR system 108. In examples, the subject identifier may also be referred to as a medical record number or master patient index (MPI). The unique subject identifier can link and update all digital data associated with the subject. The detailed description about association of the digital data with the subject will be described in later paragraphs of the document.

In some embodiments, the social network platform 106, as shown in FIG. 1, may interact with the EMR system 108 to implement a social cloud. The social network platform 106 can include one or more social network servers 110 and database servers 112 to provide real-time data updates to the EMR system 108. The social network servers 110 in communication with the database servers 112 may allow the subject to access and update or share the digital data either manual inputs or through automated data scraping and extraction techniques. The social network servers 110 may constantly interact with the EMR system 108 to provide real-time data updates associated with the subject (or associated entities such as care providers or healthcare providers). Likewise, the social network servers 110 may also provide real-time updates associated with one or more social services to the EMR system 108.

The EMR system 108, described herein, may be centralized or decentralized. In an embodiment, the EMR system 108 may be blockchain configured to allow a federated distributed access for the entities. The EMR system 108 may store the digital data related to the subjects in a digital records repository 114. The EMR system 108 may communicate with different servers and repositories such as the social network servers 110 and the database servers 112, and the private networks 102. The digital records repository 114 can store the plurality of electronic healthcare records (or the digital data referred interchangeably) including data or information related to the entities in the form of computer executable files associated with the subject containing the digital data. The digital data can be organized in such a way that facilitates local or remote information access and manipulation in the communication network 104 via a processing component 120. In some embodiments, the processing component 120 may be, but not limited to, a microprocessor, a microcontroller, or equivalent. The processing component 120 may be capable of executing instructions to process the digital data over the communications network 104. In some embodiments, the digital data corresponding to an individual subject may have been derived from medical testing or treatment or diagnostics reports. In some embodiments, the digital data may have been derived from other sources such as a research organization trial, insurance services, medical devices, or any other source. The digital records repository 114 may include a memory circuit and a processing unit for storing dynamically updating computer executable files aggregated from a plurality of changing private networks 102 such that the computer executable files contain dynamically updating digitally recorded information indicative of a set of changing subject attributes and respective changing reference values associated with the subject.

The digital records repository 114 may also include data related to different electronic or social sources such as doctor's visits, lab tests, hospital stays, clinical trials, patient problems, patients health information, patient habits, patient medical history, patient appointments, patient medical insurance, patient medical bills status, or any other information. The EMR system 108 may include or couple to other electronic or social data sources such as an HIE repository 116 and the VMR repository 118 to dynamically update information related to or from the other electronic sources. The HIE repository 116 may include electronic healthcare information related to a region, community, or hospital system. In examples, the HIE repository 116 may provide additional storage, retrieval, and manipulation of digital information such that the EMR system 108 can dynamically manage and update the digital data related to the entities. The HIE repository 116 may facilitate mobilization of digital information electronically across various repositories connected to the EMR system 108, across organizations within a region, community or a hospital. The HIE repository 116 may store information or medical records associated with the entities from disparate regions, or communities and allow to electronically move the information or the medical records among disparate health care information systems or repositories of the EMR system 108. The VMR repository 118 described herein may store electronic information related to the entities. The VMR repository 118 may be coupled to the EMR system 108 to store virtual medical records that may include a simplified, standardized electronic data designed to support interfacing to the EMR system 108 or clinical decision support systems. The present system can allow the entities to access and share or update the digital data in different sources or repositories of the EMR system 108.

The EMR system 108 may include or be coupled to an electronic record (ER) client 122 comprising a hardware device encapsulating software modules and various special purpose circuitry. The ER client 122 can be capable of monitoring, collecting, analyzing, and updating the digital data associated with the digital data sources 124. The detailed description about the ER client 122 will be provided in conjunction with FIG. 2.

Figure 2:
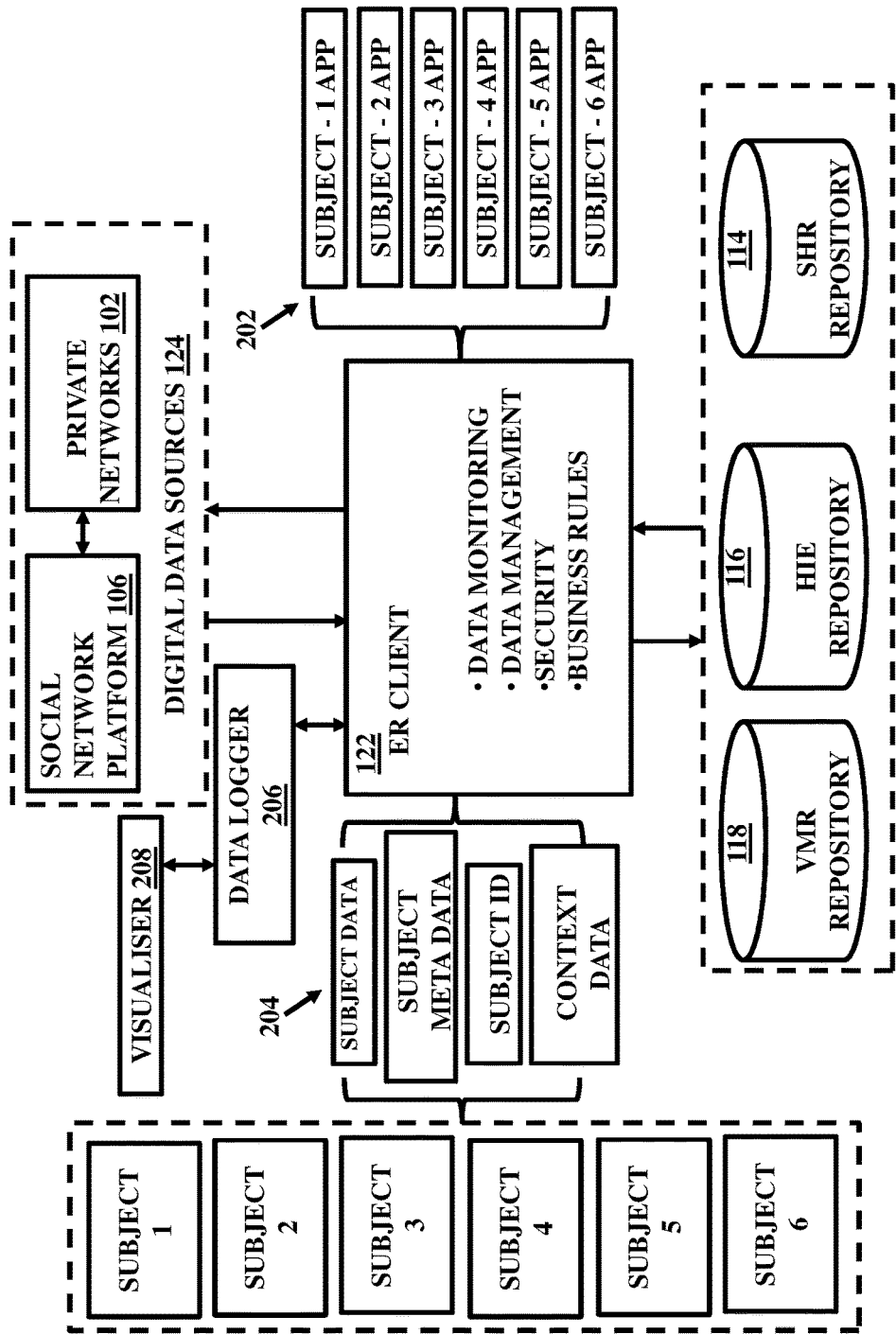
FIG. 2 illustrates generally, but not by the way of limitation, among other things, an ER client such as described in FIG. 1, in accordance with an embodiment.

FIG. 2, with reference to FIG. 1, illustrates generally, but not by the way of limitation, among other things, the ER client 122 such as described in FIG. 1, in accordance with various embodiments herein. The ER client 122 can be configured to monitor, collect, analyze, and update the digital data associated with the subject and collected from the digital data sources 124. In an example, the ER client 122 can be configured to expose a SOAP (Simple Object Access Protocol) based web-service API (Application Program Interface) that allows the digital data sources 124 to push digital information in real-time directly into the EMR system 108 such that the ER client 122 may analyze the digital data and transfer a request to the EMR system 108 to update the stored digital information in the digital records repository 114 associated with the subject. The above specified protocol is only for exemplary purposes and the present system may use any other protocol capable of managing real-time flow of digital information from various sources over the communication network 104. As used herein, the term "real-time" may refer to seconds, minutes, or hours, by the way of definition of the particular application, EMR system 108, or enterprise being controlled and the like. For example, in a certain type of enterprise, the term "real time" may refer to propagating information from the sources within a few minutes or hours. In another enterprise application, the term "real time" may refer to propagating information from the sources substantially immediately, i.e., within a few seconds.

The ER client 122 may be configured to make a wireless connection with each of the private networks 102 and configured to query ER databases associated with each of the private networks 102 for electronic records residing within the private networks 102 or other data sources 124.

The ER client 122 includes various software and hardware modules such as for example, but not limited to, data monitoring module, data management module, security module, and business rules module. The data monitoring module of the ER client 122 monitors the digital data to discover any data updates related to the subject.

The digital data may include for example, but not limited to, long term care and nursing information, labs and research information, doctor's visits, medication administration records, physician orders, emergency information resource information, hospital stays, clinical trials, patient problems, patients health information, patient habits, patient medical history, patient appointments, patient medical insurance, patient medical bills status, medical devices associated with a subject, specifications and operating parameters of the subject, or any other information pertaining to the subject. The digital information described herein can be associated with the subject with the use of the 'subject identifier' uniquely defining the subject. This may be referred to as "patient association". In accordance with some embodiments, several automated and non-automated devices, sensors, and the like devices or equipment can be used in a shared environment like a hospital, or a clinic or any other environment. These devices and sensors, and the like may be used to monitor or record health parameters or information of the subject. For example, these devices can monitor or record information about blood pressure and other conditions or status of the subject. This monitoring and recording of the subject can be performed at several distinct times. For example, a subject may arrive in a hospital in the morning and get his health information recorded or monitored at that time while a second subject arrives in the evening when his health-related information is monitored or recorded. In some embodiments, the same devices may be used for monitoring or recording purposes of several subjects. The recorded or monitored information is stored in the EMR system 108 in association with the details of the respective subjects. This may allow the EMR system 108 to know which data elements or detail corresponds to which subject. Such patient association may allow the EMR system 108 to function in a proper and accurate manner. The EMR system 108 can easily trace records for specific patients through a "patient association" technique.

The ER client 122 is configured to include and use digital information of the subject from the one or more digital data sources 124 to update the real-time digital data associated with the subject via the data management module. Various entity applications 202 specific to each subject described herein may include for example, but not limited to, patient application, clinical application, lab application, admin application, health care application, financial organization application, insurance application, research organization application, or any other entity application. The ER client 122 can be configured to use the data management module to update the real-time digital data identified by the data monitoring module. The ER client 122 may update the data and based on the information propagated from the data monitoring module of the ER client 122. The ER client 122 may use identification information 204 associated with the subject to update the corresponding entity applications 202 and the digital records. The identification information 204 described herein, may include for example, but not limited to, subject specific information such as name, age, gender, phone number, contact details, subject identifier, and the like, entity meta data such as to quickly and precisely search for desired data, entity identifier (ID) such as an entity unique identifier, entity specific contextual data such as research notes pertaining to the entity, or any other identification information. The ER client 122 may further use the identification information 204 associated with the subject to identify corresponding electronic records to be updated in the digital records repository 114. This may include, for example, a mobile phone number, IP address of a computer and any other reference associated with the subject.

The ER client 122 may send a request to the EMR system 108 to update the corresponding digital data of a subject, in accordance with the identified real-time data associated with the subject. Likewise, in some examples, the EMR system 108 may allow the ER client 122 to interact with the digital data sources 124 to monitor and update the digital data propagated to or from the social cloud or private networks or social networks. The ER client 122 identifies the real-time data and sends a request to the EMR system 108 for dynamically updating the associated digital records repository 114. The EMR system 108 may run automated monitoring software to alert the subject about the updated records and associated data.

The security module and the business rules module may implement one or more security technologies and predetermined business rules to provide secure access and updates to or from the EMR system 108 such that various subjects 1-6 can access and update their respective digital data, based on the roles and access levels, over the communication network 104, directly or indirectly via the ER client 122. In some embodiments, the ER client 122 is coupled to a data logger 206, as shown in FIG. 2. The data logger 206 is configured to retrieve data from various digital data sources 124 integrated or coupled or included to/within the EMR system 108, and log the data in the digital records repository 114. The digital records repository 114 can be contained within the EMR system 108. The data logger 206 is coupled to a visualizer 208 that is configured to retrieve the digital data from the data logger 106 or the EMR system 108 and visualize it such that a health care-specific task can be operated on it. In some embodiments, the visualizer 208 can generate visual reports that may or may not be tabulator in nature. The visualizer 208 provides an output that is simplified for a physician to make sense thereof.

Figure 3:
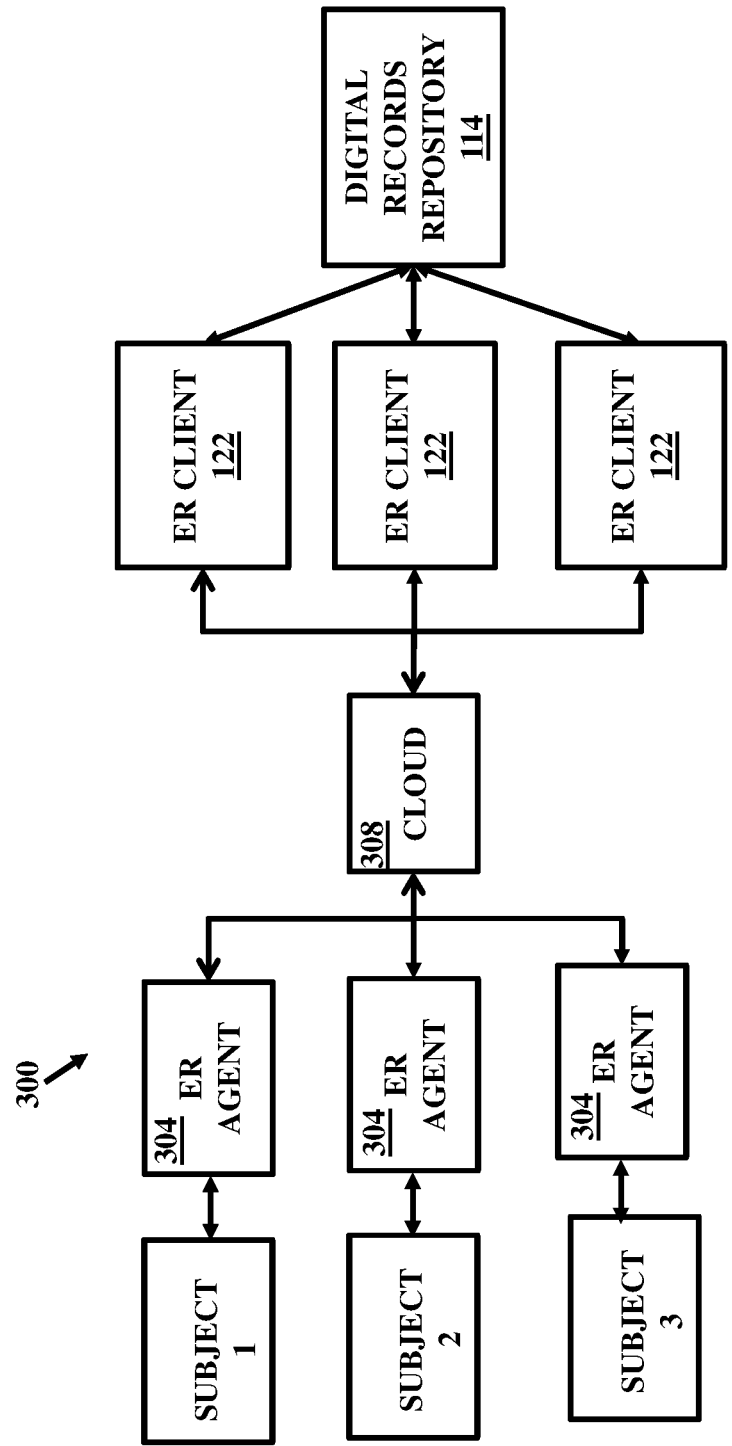
FIG. 3 is a schematic diagram that illustrates generally, but not by the way of limitation, an exemplary cloud computing architecture, in accordance with an exemplary embodiment.

FIG. 3, with reference to FIGS. 1 and 2, is a schematic diagram that illustrates generally, but not by the way of limitation, an exemplary cloud computing architecture 300, in accordance with the various exemplary embodiments herein. One or more subjects such as subjects 1-3 as shown in FIG. 3 can access their respective digital data via an ER agent 304. The ER agent 304 described herein may be a software component running on the electronic data processing system of the respective subjects 1-3 or associated entities such as a caretaker or care provider. The ER agent 304 can be a web-based agent that may allow access to the respective digital data associated with the subjects 1-3 and stored in the digital records repository 114. The web-based agent may be accessed directly or indirectly. The direct access to the web-based agent can be done by the subjects 1-3 via a respective Uniform Resource Location (URL) address for each subject 1-3. The web-based agent can also be accessed indirectly by various subjects 1-3 via a social service interface or any other third party interface. The social service described herein can be, but not limited to a service such as provided by Facebook™, Orkut™, LinkedIn™, Twitter™, and the like. In an example, the ER agent 304 may be a standalone application configured to be installed on the electronic data processing systems of the subjects 1-3 or associated entities. The ER agent 304 can be configured to provide access to the various application modules of the ER system 108, based on roles and access levels. The ER agent 304 can be communicatively connected with the ER client 122 for allowing communication between the digital data sources 124 associated with the respective subjects 1-3 and the EMR system 108.

In an example, the digital data associated with the subjects such as the subjects 1-3 may be updated from the respective digital data sources 124 via the ER agent 304 in real-time over cloud 308 facilitated by the communication network 104. The ER client 122 may monitor the real-time information updates to or from the digital data sources 124 to identify corresponding records in the digital records repository 114 to be updated. The ER client 122 may transfer a request to update one or more computer executable files associated with the subjects 1-3 in the digital records repository 114, in accordance with the propagated real-time information. Likewise, the ER client 122 may also monitor the updates to or from a social service such as the social networking platform 106 providing access to the entities associated with the subjects such as the subjects 1-3 to update the digital data over the cloud 308.

A method for dynamically updating the digital data associated with the subjects 1-3 from the digital data sources 124 in the EMR system 108, in accordance with various embodiments, can also be employed. The ER client 122 of the EMR system 108 monitors real-time information updates from the digital data sources 124 via the ER agent 304. The ER client 122 identifies one or more electronic records to be updated, in accordance with the propagated real-time information. The ER client 122 transfers a request to update the corresponding electronic records associated with the subjects 1-3 to the EMR system 108.

The methods described herein may be deployed in part or in whole through a machine that executes software programs on a server, client, or other such computer and/or networking hardware on a processor. The processor may be part of a server, client, network infrastructure, mobile computing platform, stationary computing platform, or other computing platform. The processor may be include a computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon.

Figure 4:
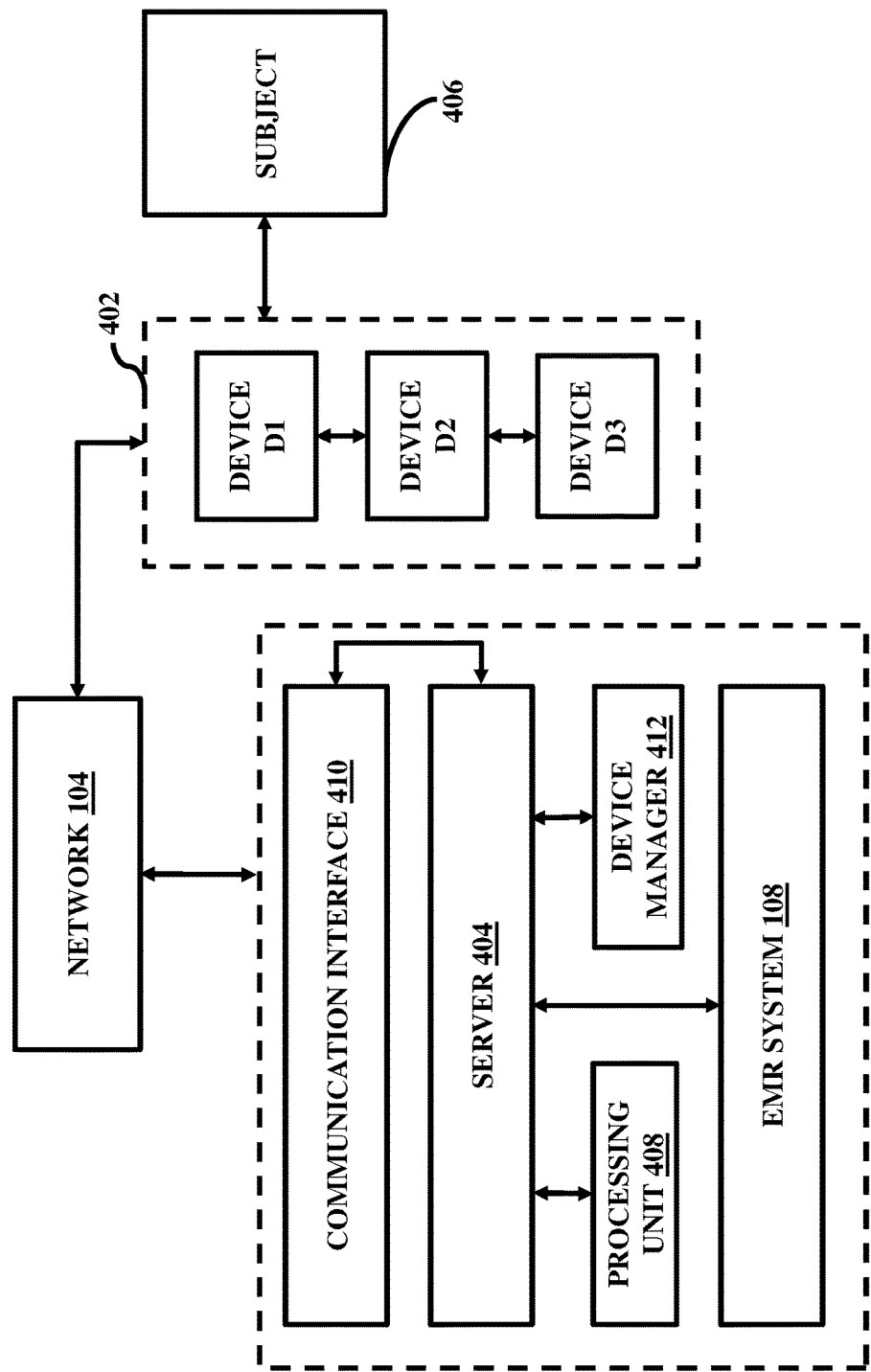
FIG. 4 illustrates generally, but not by the way of limitation, a plurality of medical devices connected with an EMR system, in accordance with an embodiment.

In accordance with some embodiments, the EMR system 108 can control other devices (D1, D2, D3) operating such as in a medical environment as shown in FIG. 4 and discussed later.

In some embodiments, the EMR system 108 and the devices can be integrated to provide the "device integration" functionality as discussed later. In some embodiments, the several devices such as D1, D2, and D3 can be integrated among themselves also while simultaneously coupled or integrated to the EMR system 108. In accordance with the device integration functionality, a device may be associated with a patient and the monitored or recorded data can be sent to the EMR system 108. The data sent may, for example, be sent from a specific device such as D1 or D2 and the like.

In accordance with some embodiments, a device such as D1 may be provided or used for a subject. In an example, if the subject is associated with the particular device D1, and when the EMR system 108 is used proximate to the device D1, the EMR system 108 automatically begins functioning in the context of the particular subject. In an embodiment, software can also be used to automatically connect to the subject simply based on the device D1 that the subject is connected or associated with. In an embodiment, each of the first medical device and the second medical device D1 and D2 may include respective (Global Positioning System) GPS-based devices such that the GPS-based devices are configured to detect geo-locations of the respective first medical device and the second medical device.

In some embodiments, the EMR system 108 may provide a functionality of device (D1, D2, and D3) coordination. In accordance with the functionality of "device coordination", based on certain kinds of information received from a device such as blood pressure from a blood pressure device, a gateway can send a command to the EMR system 108 or to other devices to do some specific task. For example, a ventilator may be required to be turned off if an X-ray is taken during a surgical procedure. So, a message is required to be sent to the gateway and other related devices to turn the ventilator off while the X-ray is taken and once the X-ray has been taken, a command to switch on the ventilator is required to be given. The device coordination functionality allows the EMR system 108 and the devices (D1, D2, and D3) to perform these tasks in a proper and coordinated way.

In still some other embodiments, the EMR system 108 may provide a functionality of device (D1, D2, and D3) control. In an embodiment, if a device such as D1 is employed at a particular location within the medical environment, the EMR system 108 may show a button to indicate the device D1, and its association with the patient. For example, if the device D1 is a BP cuff tied to a subject, the EMR system 108 may indicate the location of the cuff and the association of the cuff with the patient by providing a button on a screen or user interface of the EMR system 108 that is configured to be pressed. As soon as the button is pressed on the user interface, the EMR system 108 sends a command to the cuff invoking it to measure the BP. A physiological sensor coupled to the patient or the cuff can send the recorded or monitored data to the EMR system 108. Thus, the "device control" functionality may provide the EMR system 108 to control the devices D1, D2, and D3 coupled to the EMR system 108.

In some embodiments, software may be provided that can automatically send a command to press the button on the user interface. By pressing the button, the device can automatically perform a desired task and send the monitored or recorded digital data to the EMR system 108.

In some embodiments, the device (D1, D2, D3), can be or include a phone, a tablet, a computer or any other device that contains sensors, an accelerometer, GPS enabled devices, and the like. The various functionalities of the medical devices D1, D2, D3 are further discussed below in detail.

It must be appreciated that various embodiments as discussed above in conjunction with FIGS. 1-3 may be combined with various embodiments implementing device integration, device coordination, and device control functionalities as disclosed below in conjunction with FIGS. 4-11.

FIG. 4, with reference to FIGS. 1 through 3, illustrates a plurality of medical devices 402 (D1, D2, D3) connected with the EMR system 108 through the network 104. The EMR system 108 stores digital data or electronic medical records of a plurality of subjects electronically. The medical records may include one or more of demographic information, medical history, treatment plans, ongoing treatments, information related to allergies, and lab reports of the plurality of subjects, and the like. In accordance with some embodiments, the medical records of the plurality of subjects stored in the EMR system 108 can be obtained socially through social aware networks (social network platform) 106 linked to the respective plurality of subjects or through other private networks 102 as discussed earlier. The medical records may also be referred to as social health records herein as they may be obtained from various socially aware networks.

The EMR system 108 may be coupled to a server machine or simply a server 404. The plurality of medical devices 402 may be coupled to the server 404 either locally or remotely so as to control functioning and coordination of the plurality of medical devices 402 based on information stored in the digital records repository 114 of the EMR system 108. The digitally stored information in the form of computer executable files may be associated with the plurality of subjects. For example, the EMR system 108 may collect data about the subjects and the associated devices 402 from various socially aware networks for example social networking websites or private networks and accordingly based on the data stored in the EMR system 108 can control and coordinate functioning of the devices 402. The stored data may be updated by the ER client 122 in real time. In an embodiment, the plurality of medical devices 402 may be integrated among themselves and also with the server 404. In an embodiment, the functioning of the plurality of medical devices 402 may be controlled or coordinated with respect to one another by the server 404. In an embodiment, the functioning of the medical devices 402 may be coordinated or controlled with respect to one another in a defined sequence. For example, the device D2 may operate after device D1 stops functioning for a defined period of time. The device D3 may operate only after D2 stops functioning for a defined period of time. Even more than one device can operate simultaneously based on the defined sequence by the server 404. The defined sequence can be determined by the server 404 based on for example information pertinent to a subject associated with the plurality of medical devices 402, information about the devices 402, functioning of the devices 402, medical condition of the subject, and level of requirement of the devices 402 for the subject under the given medical condition of the subject.

The server 404 may send instruction to the plurality of medical devices 402 associated with the subject such as subject 406 for proper coordination and control of the devices 402. The server 404 may include or be coupled to a processing unit 408. The server 404 may further include a communication interface 410 to communicate with the medical devices 402.

In an embodiment, the EMR system 108 and the server 404 may be deployed in a hospital facility to control and coordinate with medical devices associated with subjects in the entire hospital. In such embodiments, the EMR system 108 may be connected to hospital information systems to socially collect digital data from various information sources within the hospital. The EMR system 108 may further receive medical records associated with the subjects from outside the hospital environment through for example various socially aware networks or private networks. The socially aware networks may include various social networking websites that the subjects may be associated or registered with. The EMR system 108 may be accessed by authorized users of the hospital facility through a web based platform. In an embodiment, the EMR system 108 and the server 404 may be deployed to communicate with several hospital facilities and organizations such that the EMR system 108 may store information pertinent to subjects and medical devices of the entire hospital facilities and the organizations.

In an exemplary embodiment, the server 404 may connect with a plurality of medical devices in a hospital facility or any other medical environment even including multiple hospital facilities and organizations and detect and locate a medical device in the health care environment, initialize with the medical device and after initialization may remotely network with the medical device such that the EMR system 108 may be able to transmit and receive information from the medical device. For example, this may be done by connecting the EMR system 108 and the server 404 to Internet or other communication network or communication system.

In an exemplary embodiment, the server 404 can remotely monitor and diagnose the plurality of medical devices 402 associated with the subject 406. The server 404 can allow remote monitoring and diagnostics of a remotely located device from among the plurality of medical devices 406 once the medical device has been located and analyzed by the server 404 and relevant details about the device and the subject 406 associated with device are obtained and stored in the EMR system 108. In an example, the server 404 may connect to any of the plurality of medical devices 402 located within any health care facility and/or outside health care facility.

In an embodiment, the server 404 may be coupled to a device manager 412. The device manager 412 may be configured to manage device information corresponding to each of the plurality of medical devices and associate the information with respective subjects. For example, the device manager 412 may be responsible for managing the information of the devices D1, D2, and D3 and associate this information with the subject 406. In this manner, the processing unit 408 along with the device manager 412 can perform tasks such as monitoring and coordinating and controlling of the medical devices 402 in a health care facility. In some embodiments, the device manager 412 may be configured to detect newly connected medical devices or any updates in the existing medical devices associated with an already registered subject with the EMR system 408. For example, the device manager 412 can detect and locate a medical device D1 and identify the medical device D1 and authenticate it and provide an administrator or privileged access to the information relevant for the device D1 in the EMR system 108. The relevant information may for example be information pertinent to other medical devices such as D2 and D3 that coordinate with the newly detected medical device such as D1.

In accordance with various embodiments, a system is provided that is configured to be communicatively coupled with the EMR system 108, server 404, and the plurality of medical devices 402. The system may facilitate communication between the server 404 and the plurality of medical devices 402. The system may be responsible for managing the medical devices 402 associated with the subject 406 and facilitate coordinated functioning and integration and control of the plurality of medical devices 406 by providing a channel therethrough. The system is described later in conjunction with FIG. 5 below. In an embodiment, this system can be integrated within the server 404 or with the EMR system 108.

In accordance with some embodiments, the devices 402 can include, for example, a blood pressure (BP) cuff, X-ray machine, a ventilator, Electrocardiogram (ECG) device, radiotherapy device, dosing controller, medical resonance therapy related device, and the like devices.

Figure 5:
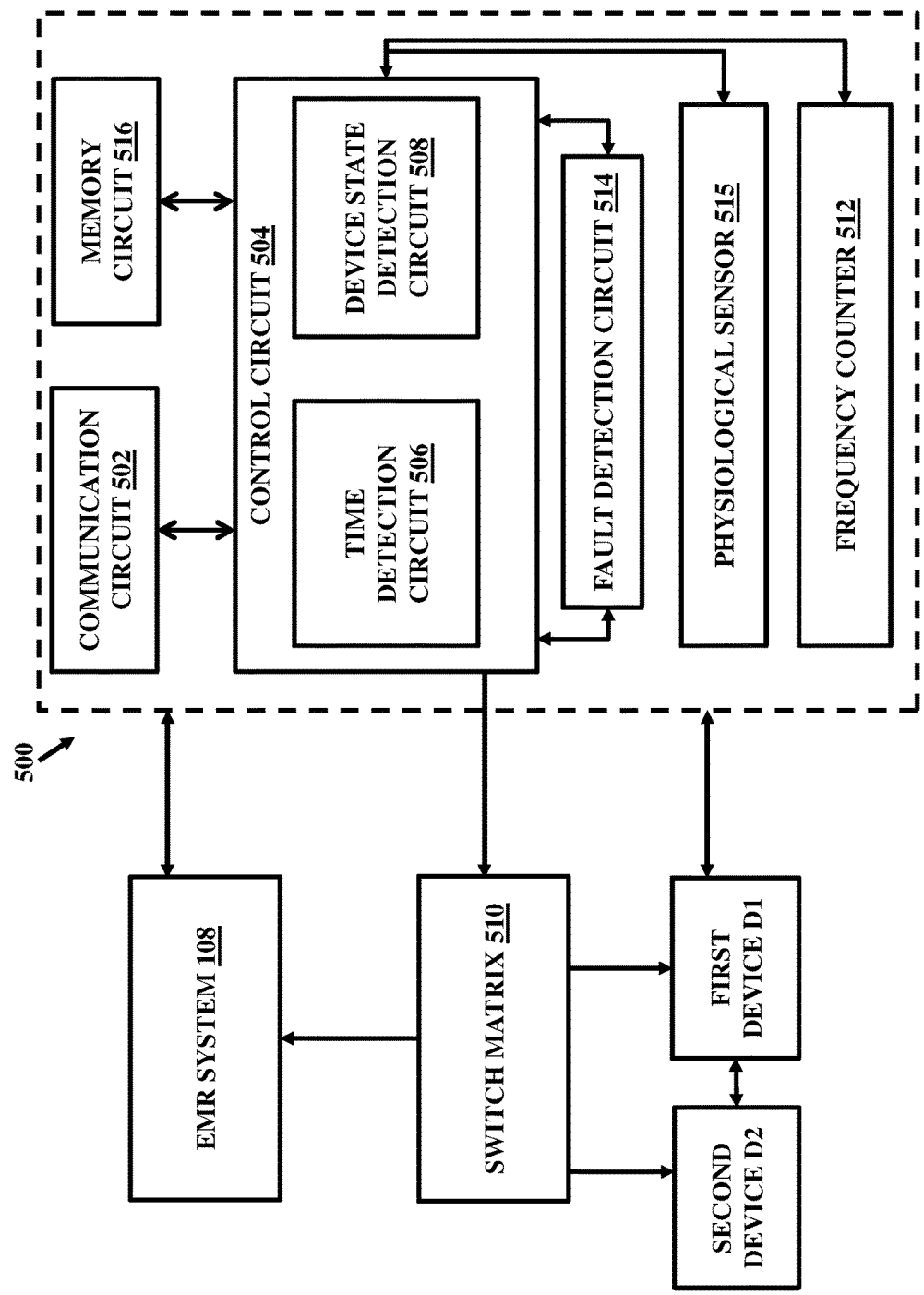
FIG. 5 illustrates, generally but not by the way of limitation, a system for facilitating coordination and control among a plurality of medical devices, in accordance with an embodiment.

FIG. 5, with reference to FIGS. 1 through 4, illustrates a system 500 for facilitating coordinated functioning of the plurality of medical devices 402 over the network 104. The system 500 may be coupled to the server 404 and the plurality of medical devices 402. The system 500 may facilitate communication between the server 404 and the plurality of medical devices 402. The system 500 may manage the medical devices 402 associated with the subject 406 and facilitate coordinated functioning and integration and control of the plurality of medical devices 402 by providing a channel therethrough.

The system 500 may include a communication circuit 502, and a control circuit 504. The communication circuit 502 may be configured to receive an input from the server 404 or the processing unit 408 coupled to the server 404. The input may be indicative of an action or a task to be performed by a first medical device such as D1 from among the plurality of networked medical devices 402. In an embodiment, each of the plurality of medical devices 402 may perform a unique task and each of the tasks performed by the plurality of medical devices 402 may be coordinated and dependent with respect to one another. The interdependence may be known to the server 404 and information about the interdependence of the tasks may be stored in the EMR system 108 in association with subject information corresponding to the medical devices 402. For example, a particular task performed by the first medical device D1 may not be desired along with the second task performed by the second medical device D2. In such cases, the server 404 sends the instruction to the system 500 which is received by the communication circuit 502 as the input. The received input by the communication circuit 502 provides a guidance that allows the medical devices 402 to function in a defined and desired manner and in accordance with the interdependence already known and stored in the EMR system 108. The interdependence may be decided by doctors or experts or persons treating the subject, or based on medical facts. The subject or the doctors or the persons treating the subject may convey the interdependence to the EMR system 108 through various channels such as through the socially aware networks 106, private networks 102, and the like. In an embodiment, the information about tasks interdependence may be automatically updated with the EMR system 108. In an embodiment, the EMR system 108 may automatically determine the information about the tasks interdependence as and when any medical device is registered with the EMR system 108 in association with a subject. The EMR system 108 may for example receive device related information and accordingly map the device information with other coordinating medical devices to define the interdependence. Once, the task interdependence is determined and known to the server 404, the functioning of the medical devices 402 may be coordinated and controlled accordingly based on the interdependence. The terms 'task' and 'action' are used herein throughout the draft interchangeably without any limitations.

The communication circuit 502 may be configured to send an instruction to the first medical device D1 to initiate the first task by the first medical device D1. The instruction may also include information about the details of the first medical device D1. In an embodiment, when the first medical device D1 functions for more than one subject, the instruction may also include information of the subject 406 associated with the first medical device D1. The information about the first medical device D1 and the subject 406 corresponding to the first medical device D1 may be stored in and retrieved from the EMR system 108.

The control circuit 502 may be configured to monitor the task performed by the first medical device D1 and receive an update periodically. In an event of a requirement of a second task performed by the second medical device D2, the system 500 may enquire the server 404 about interdependence of the first task and the second task and about the interdependence of the first medical device D1 and the second medical device D2. In an embodiment, the server 404 may retrieve the information about interdependence from a lookup table stored in the EMR system 108. The processing unit 408 may process information about the interdependence. In case, there is a conflict between the first task by the first medical device D1 and the second task by the second medical device D2, the server 404 may send the information about conflict to the system 500 accordingly. In another embodiment, the system 500 may not enquire about the interdependence rather instructions for performance or non-performance of the tasks are sent by the server 404 to the system 500.

The control circuit 504 may be configured to instruct the first medical device D1 to pause performing the first task for a defined period of time based on an instruction from the server 404 after determining tasks' interdependence information. The instruction may also be indicative of the second task to be performed by the second medical device D2. The predefined period of time may depend on various factors such as patient information, nature and type of the first and second medical devices D1 and D2, functioning and behavior of the first and second medical device D1 and D2, medical condition of the subject 406, degree of requirement and necessity of the first and second tasks for the subject 406 in light of the current medical condition of the subject 406. For example, if the second task is extremely necessary and vital for the current medical condition of the subject 406, the instruction may indicate to perform the second task for a time necessary to control criticality of the medical condition of the subject 406.

The control circuit 504 may include a time detection circuit 506 configured to monitor the defined period of time during which the first medical device D1 pauses performing the first task and the second medical device D2 performs the second task. The time detection circuit 506 may be configured to generate a signal upon completion of the defined period of time. The signal may be indicative of resuming the first task by the first medical device D1 and stopping of the second task by the second medical device D2. The time detection circuit 506 may be configured to initialize at a zero time value and monitor the passage of time until the monitored time equals the defined period of time after which the signal is generated indicative of the resuming of the first task by the first device D1 and stopping of the second task by the second device D2.

The control circuit 504 may include a device state detection circuit 508 coupled to the time detection circuit 506 and configured to identify an operating state of the plurality of medical devices 402. The operating state may be defined by performance or non performance of the medical devices 402. For example, the performance of the first medical device D1 may define a first operating state and non-performance of the first medical device D2 may define a second operating state of the first medical device D1. Similarly, the performance of the second medical device D2 may define a first operating state and non-performance of the second medical device D2 may define a second operating state of the second medical device D2. Based on interdependence between the first and the second tasks, the operating states of the first medical device D1 may depend on the operating states of the second medical device D2. For example, if the interdependence suggests a conflicting situation between the first and the second tasks, the first operating state of the first medical device D1 may not occur during occurrence of the first operating state of the second medical state D2. Therefore, either of the first and second medical devices D1 and D2 has to be in a non-performing operating state during the defined period of time.

The system 500 may include a switch matrix 510 that is configured to cause a switching action of the operating states. For example, the switching matrix 510 may be configured to cause switching of the first and the second medical devices D1, D2 from a performing operating state to a non-performing and from a non-performing state to a performing state based on an instruction from the control circuit 504. In an embodiment, the switch matrix 510 may cause switching of the operating states of one or more of the first medical device D1 and the second medical device D2 upon receipt of the instruction from the control circuit 504. In an embodiment, the switch matrix 510 may cause switching of the operating states of one or more of the first medical device D1 and the second medical device D2 upon receipt of the signal generated by the time detection circuit 506 that is indicative of completion of the defined time and of resuming the first task and stopping the second task. The resuming of the first task requires a switching of the non-performing state of the first medical device D1 to a performing state of the first medical device D1. The stopping of the second task by the second medical device D2 requires switching of the performing state to the non-performing state of the second medical device D2 by the switch matrix 510.

The control circuit 504 may include or be coupled to a frequency counter 512 configured to determine frequency of switching of operating states of the medical devices 402. For example, the frequency counter 512 may be configured to determine frequency of switching of the first medical device D1 from a performance state to a non-performance state of the first action and vice versa. Similarly, the frequency counter 512 can be configured to determine frequency of switching of operating states of other medical devices such as D2. In an embodiment, the frequency counter 512 may generate an output indicative of a current frequency of switching of an operating state of a medical device such as D1 and D2. The frequency counter 512 may further be configured to map the current frequency of switching with a threshold frequency established by the EMR system 108 based on a set of physiological parameters in association with the information associated with the subject 406. In an embodiment, the physiological parameters may include vital signs of the patient 406 and continuously detected by physiological sensors as discussed hereafter. The relevant information of the subject 406 may include for example without limitations degree of necessity of switching of the operating states of one device with respect to other device for the subject 406, age, gender, medical condition and other such subject-specific information. For example, an aged person in a critical condition may not tolerate frequent putting off of a ventilator machine and therefore a person responsible for patient care may not allow switching of the ventilator to an off state very frequently beyond a threshold limit. In an embodiment, the threshold limit may be defined for a unit period of time. For example, switching of a subject's ventilator from an on to off state may in certain conditions be not allowed beyond three times a day with each not more than 15 minutes. The frequency counter 512 may further be configured to reject the switching of the operating state of the first medical device D1 or the second medical device D2 if the current frequency of switching equals the threshold frequency for the respective medical devices D1, D2. For example, upon receipt of the instruction by the communication circuit 502 to switch the first medical device D1 from the performing state to the non-performing state for the defined period of time, the request for switching may be rejected by the frequency counter 512 if the current frequency already reached the threshold frequency.

In accordance with various embodiments, there should be a consistency in output generated by the time detection circuit 506 and the device state detection circuit 508. For example, upon completion of the defined time and its detection by the time detection circuit 506, there should be a change in an operating state of the first medical device D1 from a non-performance to a performance state. Therefore, both the time detection circuit 506 and the device state detection circuit 508 should lead to a state of shift which should be consistent. In an event of an inconsistency, a fault may occur. The system 500 further includes a fault detection circuit 514 configured to generate a signal indicative of a fault if the device state detection circuit 508 does not detect a change in the operating states of either of the first and second medical devices D1, D2 upon receipt of the instruction from the control circuit 504 to initiate or pause the first action and upon generation of the signal by the time detection circuit 506 to stop the second action and resume the first action on completion of the defined time. The signal generated by the fault detection circuit 514 may be transmitted to the EMR system 108 through the communication circuit 502 to determine optimal states of the first medical device D1 and the second medical device D2 upon detection of the failure. The optimal states can be other than what is initially instructed by the server 404 to the system 500 for example to switch the first medical device D1 to non-performing state and to switch the second device D2 to performing state for the defined time. The server 404 may be configured to determine the optimal states of the first and second medical devices D1, D2 based on the information of the subject 406 associated with the first medical device D1 and the second medical device D2. For example, the server 404 may determine an alternative treatment technique to fulfill the requirement that is not achieved because of the detection of the fault. In an embodiment, the server 404 can send an instruction to the system 500 to guide a subject caretaker to manually attend the subject 406. There can be several reasons for the fault. One reason may be malfunctioning of the first and/or the second medical device D1, D2. In such cases, the defaulted medical device may be replaced. Another reason may be a rejection by a medical device to follow the instruction sent by the control circuit 504 or the switch matrix 510 to switch the operating states. The rejection may occur because at least one medical device may be authorized to reject the instruction in some embodiments. For example, the first medical device D1 may be authorized to reject to pause performing the first task based on the instruction received from the control circuit 504. The rejection by the first medical device D1 influences the second task to be performed by the second medical device D2. In such cases, the first medical device D1 may coordinate with other medical devices but may not be completely controlled by the system 500 to function in a defined manner. This is because the first medical device D1 is provided a privilege to reject the request for switching the state. In other embodiment, however, the first medical device D1 may not be authorized to reject the request for switching and may be completely controlled by the system 500. In an event of rejection, the server 404 may be informed about the rejection to determine an alternative action for the second medical device D2 or an alternative medical device to replace the need of the second medical device D2 by a third device to perform a third task (that may be similar or alternative to the second task) in a manner that the first medical device D1 has no objection with the third task. For example, the first medical device D1 may not reject because the third action may be defined in a manner that it may not need pausing of the first task, and the first and the third tasks may be performed simultaneously because of a specific interdependence between them. The server 404 may in some embodiments determine the alternative tasks or medical devices with the use of the interdependence information saved in the EMR system 108 or in a memory of the system 500.

In some embodiments, the system 500 may include a physiological sensor 515 configured to be coupled to the subject 406 to identify a set of physiological characteristics of the patient 406 during performance and non-performance and/or before/after switching operations of the first and the second medical devices D1, D2. The physiological characteristics may be one or more of blood pressure, heart beat, respiratory rate, body temperature, and glucose level, and other such characteristics without limitations. In an example, the switching of the operating state for example from performance to non performance or vice versa of the first and second medical devices D1, D2 based on the instruction received from the server 404 may be rejected upon indication of a change in the physiological characteristics beyond respective threshold values corresponding to each of the physiological characteristics. The physiological sensor 515 may determine indicative values of the one or more physiological characteristics of the subject 406 before switching and after switching, and upon a change in the characteristics beyond the threshold limit, the request for switching from the server 404 may be rejected. In an embodiment, the physiological sensor 515 may forecast possible changes that may occur in the physiological characteristics after switching based on the subject-specific information, information about the characteristics and other medical information stored in the system 500. Based on the determined values of the physiological characteristics before switching and possible forecast values after switching, the request for switching may be rejected if the change in the values of the physiological characteristics is beyond the threshold limit. In an embodiment, the physiological characteristics may include without limitations blood pressure, heart beat, respiratory rate, body temperature, and glucose level. The physiological sensor 515 may be coupled to the subject 406 for monitoring the various physiological characteristics. In an embodiment, the physiological sensor 515 may be implanted within a patient body. In an embodiment, the physiological sensor 515 may be implanted as a standalone component. In another embodiment, the physiological sensor 515 may be implanted as a component of another implantable device already implanted in the body such as a pacemaker or a defibrillator, or any other implantable device.

In an embodiment, the threshold values of the physiological characteristics may be determined and updated regularly by the processing unit 408 of the server 404 and stored in the EMR system 108 in real time. The updating of the threshold values can depend on an update in subject-specific information such as age, disease, gender, and height-weight index of the subject 406 and the like information and are communicated to the system 500 for storage locally within the system 500 in real time. The system 500 may store information about the threshold values of the physiological characteristics in a memory circuit 516. The memory circuit 516 may further store the information received from the processing unit 408 coupled to the server 404 and subject-specific information obtained from the EMR system 108.

In an embodiment, the EMR system 108 may be configured to store medical records of a plurality of subjects including the subject 406. The medical records may be associated with the plurality of subject and may be obtained socially through the social aware networks 106 or other private networks 102 linked to the respective plurality of subjects. For example, the subject 406 may register him with a social networking website and upload his medical information and the server 404 may retrieve information from the website and store in the EMR system 108. The EMR system 108 may function as a two way communication database which can access digital federated records from the socially aware networks 106 or private networks 102 of the subjects for collecting and collating the digital medical records and also serve as a repository to be accessed by the subjects from anywhere to view and access their digital records at a single location. In various embodiments, the digital medical records may include one or more of demographic information, medical history, treatment plans, ongoing treatments, information related to allergies, and lab reports of the plurality of subjects.

Figure 6:
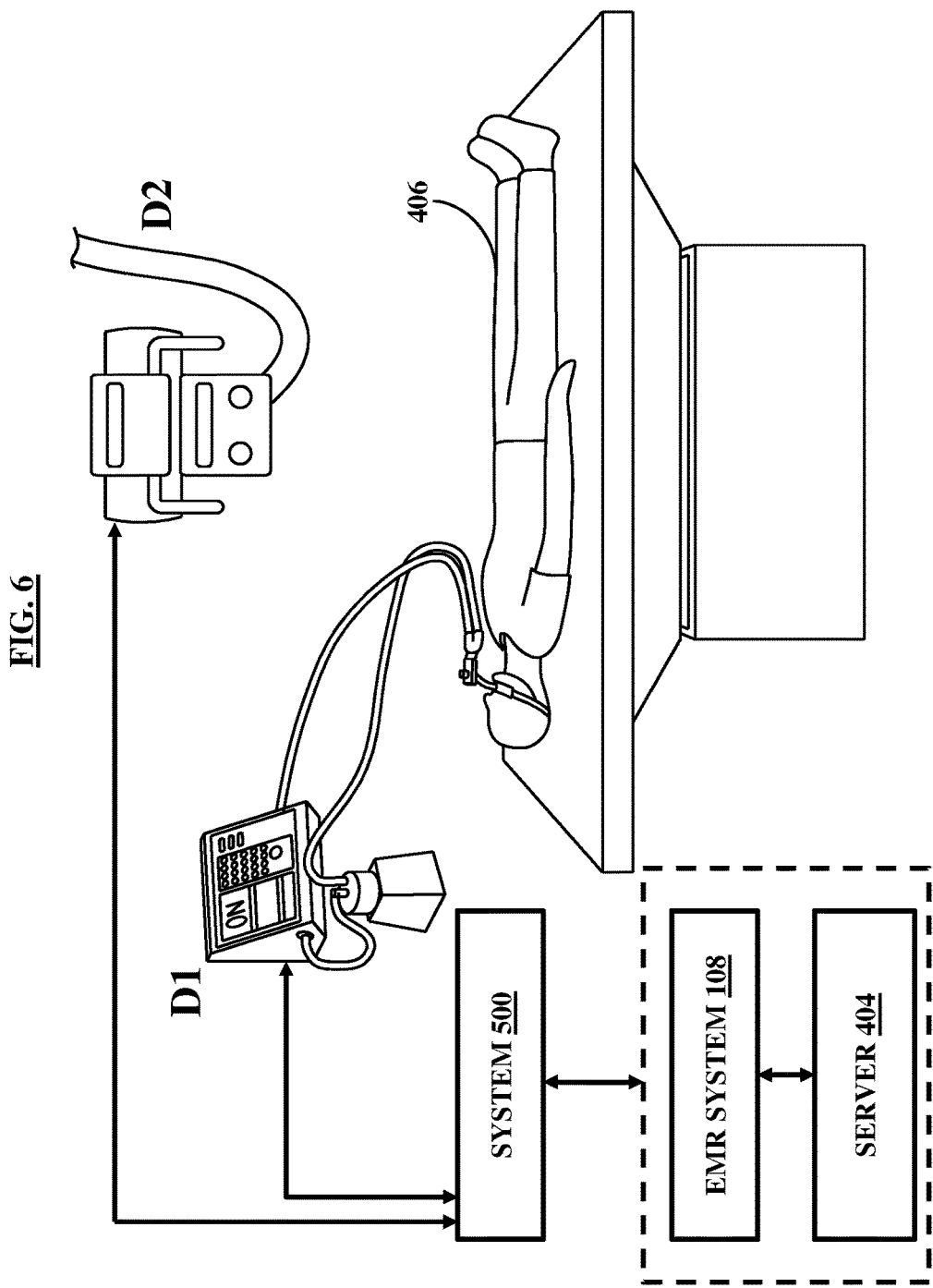
FIG. 6 illustrates, generally but not by the way of limitation, an example of a first medical device and a second medical device coordinating in a network before switching their operating states, in an embodiment.

FIG. 6, with reference to FIGS. 1 through 5, illustrates an exemplary embodiment of the medical devices D1 and D2 coordinating through and controlled by the system 500. As shown, the first medical device D1 is a ventilator and the second medical device D2 is an X-ray machine. The ventilator D1 is shown in the first operating state which is defined by performing the first task that is providing artificial life support to the patient 406. The second medical device D2 is shown in the second operating state which is defined by non-performing the second task by the second medical device D2. The first task may be dependent on the second task. As shown, the interdependence between the first task and the second task is such that when the first medical device D1 operates to provide artificial ventilation, the second medical device D2 stays off. Therefore, the X-ray D2 machine is shown as in an off state or in the second state of non-performing of the task of radiating to capture an X-ray. This interdependence may be established based on well known medical reasons that an X-ray should not be taken while a patient is on a ventilator machine. Similarly, in some other examples, the interdependence can be established based on various other factors also such as discussed above.

Figure 7:
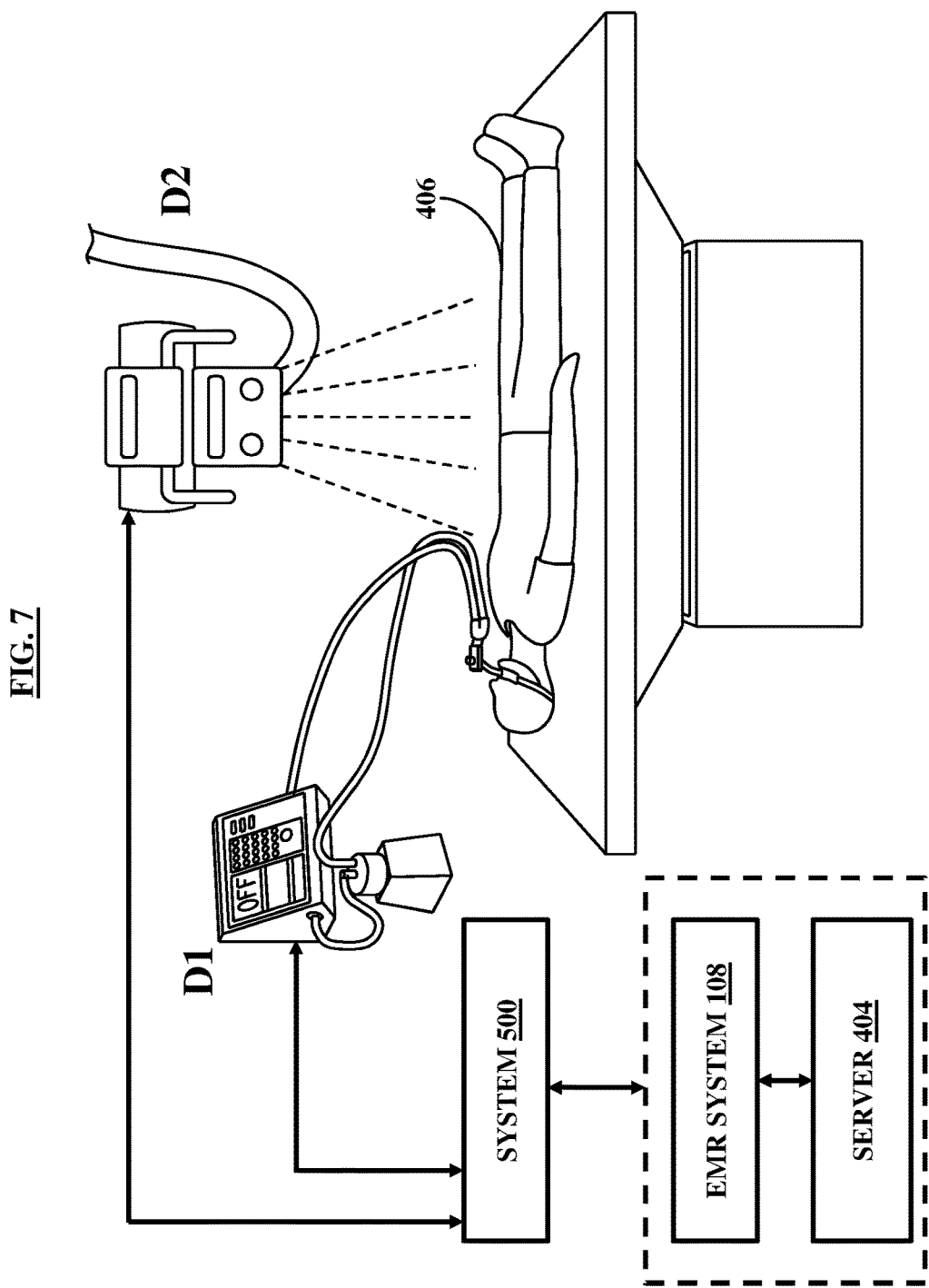
FIG. 7 illustrates, generally but not by the way of limitation, an example of the first medical device and the second medical device coordinating in the network after switching their operating states, in accordance with an embodiment.

FIG. 7, with reference to FIGS. 1 through 6, shows the exemplary embodiment of FIG. 6 after switching of the operating state of the first medical device D1 based on the instruction received from the switch matrix 510 or the control circuit 504. The interdependence between the ventilator D1 and the X-ray machine D2 is of the type that X-ray machine D2 will operate only when the ventilator D1 is off. Therefore, the instruction of switching includes sending a request to the ventilator D1 (first medical device) to pause delivering the artificial ventilation and sending a request to the X-ray machine D2 (second ventilator) to activate its task that is delivering radiation for capturing the X-ray. The FIG. 7 therefore shows the ventilator D1 in an off state for the defined time and the X-ray machine D2 in an on state for the defined time. The defined time may be based on various factors as discussed above. One of them may be the level of necessity of the ventilation by the patient 406. For example, if the subject 406 is under critical condition, ventilation may be paused for a very short period of time only. If the subject 406 is in an extremely critical condition, then the task of taking the X-ray may altogether be postponed or rejected. The server 404 may be updated accordingly in case of the postponement or rejection. The EMR system 108 may maintain a log of such rejections or postponements for the patient 406 so as to accordingly refine the interdependence of the various tasks performed by various medical devices associated with the subject 406 for future use. For example, in the future for a defined time such as three days, the system 500 may not instruct the X-ray machine D2 to operate in view of the refined interdependence established and stored in the EMR system 108 when the ventilator D1 is on.

FIG. 8, with reference to FIGS. 1 through 7, illustrates exemplary listing of interdependence in the look up sheet maintained by the EMR system 108. It must be noted that the interdependences are dynamic in nature and are updated after periodic intervals or in real-time. The real time updating can be done with the use of the ER client 122 discussed in FIG. 2. As shown, in examples, when D1 performs its task, D2, D3, and D6 cannot perform or operate in their performing state. When D2 operates in the performing state, D1, D3, and D8 cannot perform. When D3 performs D1, D2, and D9 cannot operate to perform. When D4 performs, D10, and D12 cannot perform. When D4 performs, D13, and D16 remain uninfluenced that is whether D13 or D16 or both perform or not, they do not affect operating state of the D4. When D2 performs, D4 has to perform.

In some embodiments, priority of performance by different medical devices may be established. For example, if the device D1 cannot perform with the devices D2, D3, and D6, then which devices(s) should perform with a higher priority. This may be determined dynamically based on several factors for example as discussed above including without limitation subject current medical condition, affect of performance or non-performance of a device on the subject medical condition, nature and functioning of the devices and their relationship with the medical condition of the subject, and the like. For example, if it is determined that D2 is more needed by the subject and gets a higher priority over D1, then D1 will be put in an off state that is non-performing state and D2 starts performing. A device that may possess a higher priority with respect to a particular device may possess a lower priority with respect to another device.

It must be appreciated that though the above discussion includes various embodiments that involve the use of two medical devices D1 and D2, it must be appreciated that more than two medical devices may also be employed equally without limiting the embodiments herein. For example, the system 500 may facilitate coordinated functioning of the plurality of devices (two or more than two) coupled to the system 500. The EMR system 108 may store the digital medical records (interchangeably referred to as or digital data without limitations) of the subject 406 and information related to a sequence of operations to be performed by the plurality of the medical devices based on interdependence among the plurality of the medical devices, identification information of the devices, and subject-specific information. The server 404 may use the stored information to guide the system 500 to instruct the plurality of devices accordingly in the defined sequence. It must be appreciated that the though the above discussion and the figures include one subject associated with medical devices, several subjects each associated with one or more devices may also be coordinated and controlled accordingly without any limitation.

Figure 9:
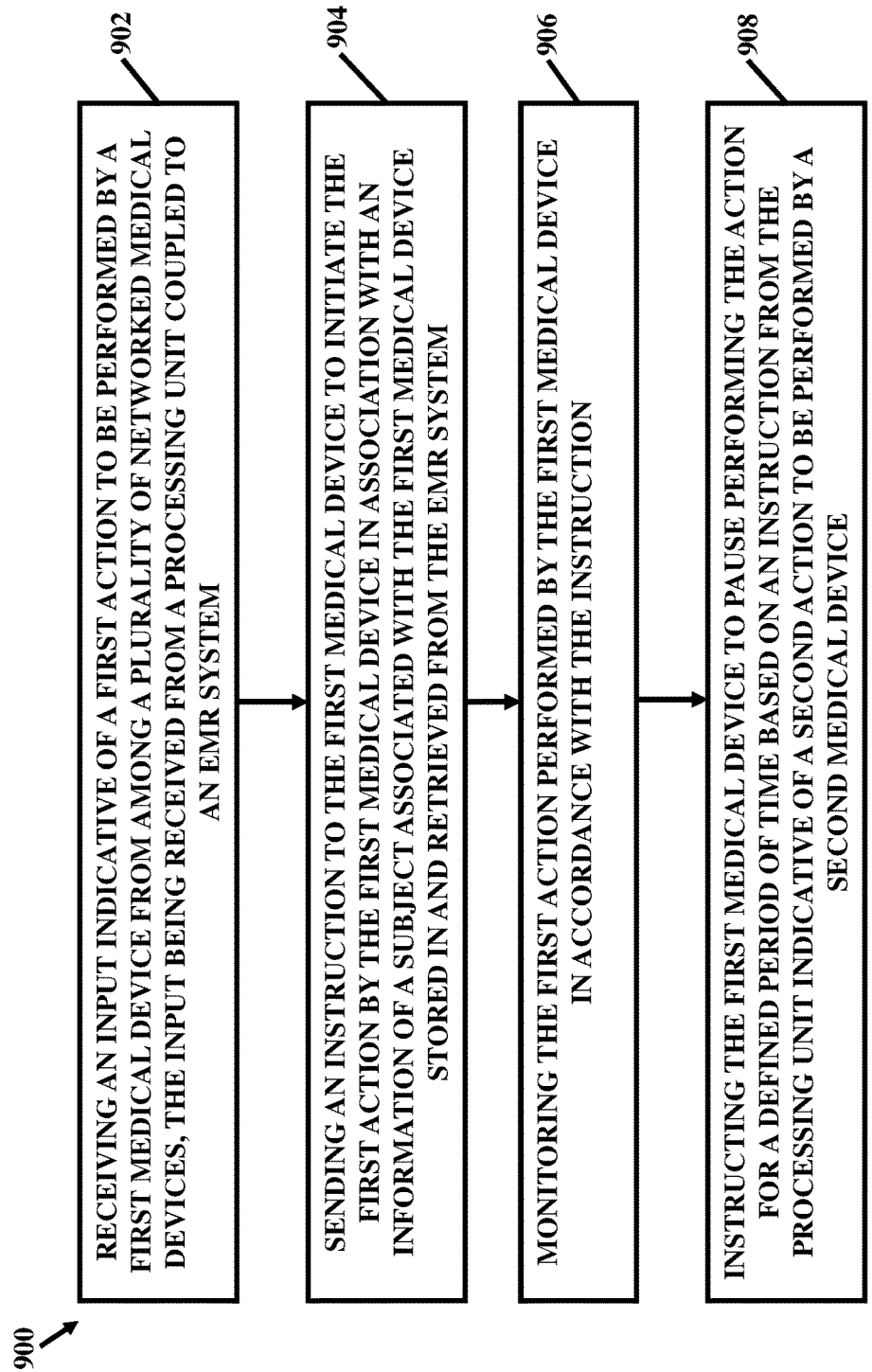
FIG. 9 illustrates a method for facilitating coordinated functioning of a plurality of medical devices, in accordance with an embodiment.

FIG. 9, with reference to FIGS. 1 through 8, illustrates a method 900 for facilitating coordinated functioning of the plurality of medical devices over the network 104. At step 902, the method 900 includes receiving the input indicative of the first action to be performed by the first medical device D1 from among the plurality of networked medical devices 402. The input is received from the server 404 coupled to the EMR system 108. At step 904, the method 900 includes sending the instruction to the first medical device D1 to initiate the first action by the first medical device D1 in association with the information of the subject 406 associated with the first medical device D1 stored in and retrieved from the EMR system 108. At step 906, the method 900 includes monitoring the first task performed by the first medical device D1 in accordance with the instruction. At step 908, the method 900 includes instructing the first medical device D1 to pause performing the first task for the defined period of time based on the instruction from the server 404 indicative of the second action to be performed by a second medical device D2.

In an embodiment, the method 900 may further include monitoring the defined period of time during which the first medical device D1 pauses performing the action, and the second medical device D2 performs the second action. The method 900 may include generating a signal upon completion of the defined period of time by the time detection circuit 506. The signal may be indicative of resuming the first action performed by the first medical device D1 and stopping of the second action performed by the second medical device D2. The method 900 may further include detecting an operating state of the second medical device D2, by the device state detection circuit 508, which defines performance or non performance of the second action by the second medical device D2 during the defined time period. The operating state of the first medical device D1 that defines performance or non performance of the first medical device D1 may be based on the operating state of the second medical device D2. The method 900 may also include determining the interdependence between the operating states or the tasks performed by the first medical device D1 and the second medical device D2. The method 900 may also include switching the operating states of the one or more of the first medical device D1 and the second medical device D2 upon receipt of the instruction from the controller circuit 504 and upon generation of the signal by the time detection circuit 506. The method 900 may also include generating a signal indicative of a fault by the fault detection circuit 514 if the device state detection circuit 508 does not detect a change in the operating states of either of the first and second medical devices D1, D2 upon receipt of the instruction from the controller circuit 504 to initiate or pause the first action and upon generation of the signal by the time detection circuit 506 to stop the second action and resume the first action on completion of the defined time.

In an embodiment, the method 900 may employ the plurality of medical devices 402 including even more than two medical devices. The method 900 may include in such cases determining a sequence of operations performed by the plurality of medical devices 402. The sequence of operations may depend on the interdependence of the tasks performed by the plurality of the medical devices 402. In cases of conflict between at least any two tasks, the method 900 may also include determining a priority task to be performed over other interdependent tasks. The priority may be determined based on various parameters as discussed above.

In an embodiment, the method 900 may include identifying measures or values of physiological characteristics of the subject 406 before switching an operating state of a medical device D1, D2. The method 900 may further include identifying measures or values of physiological characteristics of the subject 406 after switching the operating state of the medical device D1, D2. The method 900 may further include determining a change in the measures of the physiological characteristics and mapping the measures with the threshold values of the physiological characteristics under defined conditions. The method 900 may include rejection switching of the operating state upon determining the change as exceeding the threshold level of the physiological characteristics. For example, if the switching involves putting a ventilator in an off state for thirty minutes, the method 900 may determine the change either after switching for a short time or forecasting an affect of putting the ventilator in the off state without actually putting it off. If the change is unacceptable for example of the heart beat goes extremely down below the threshold level, the request for switching the ventilator in the off state may be rejected.

It must be appreciated that various embodiments discussed in conjunction with FIGS. 1-3 may be combined with various embodiments implementing the device integration, device coordination, and device control functionalities as disclosed in conjunction with FIGS. 4-11.

Figure 10:
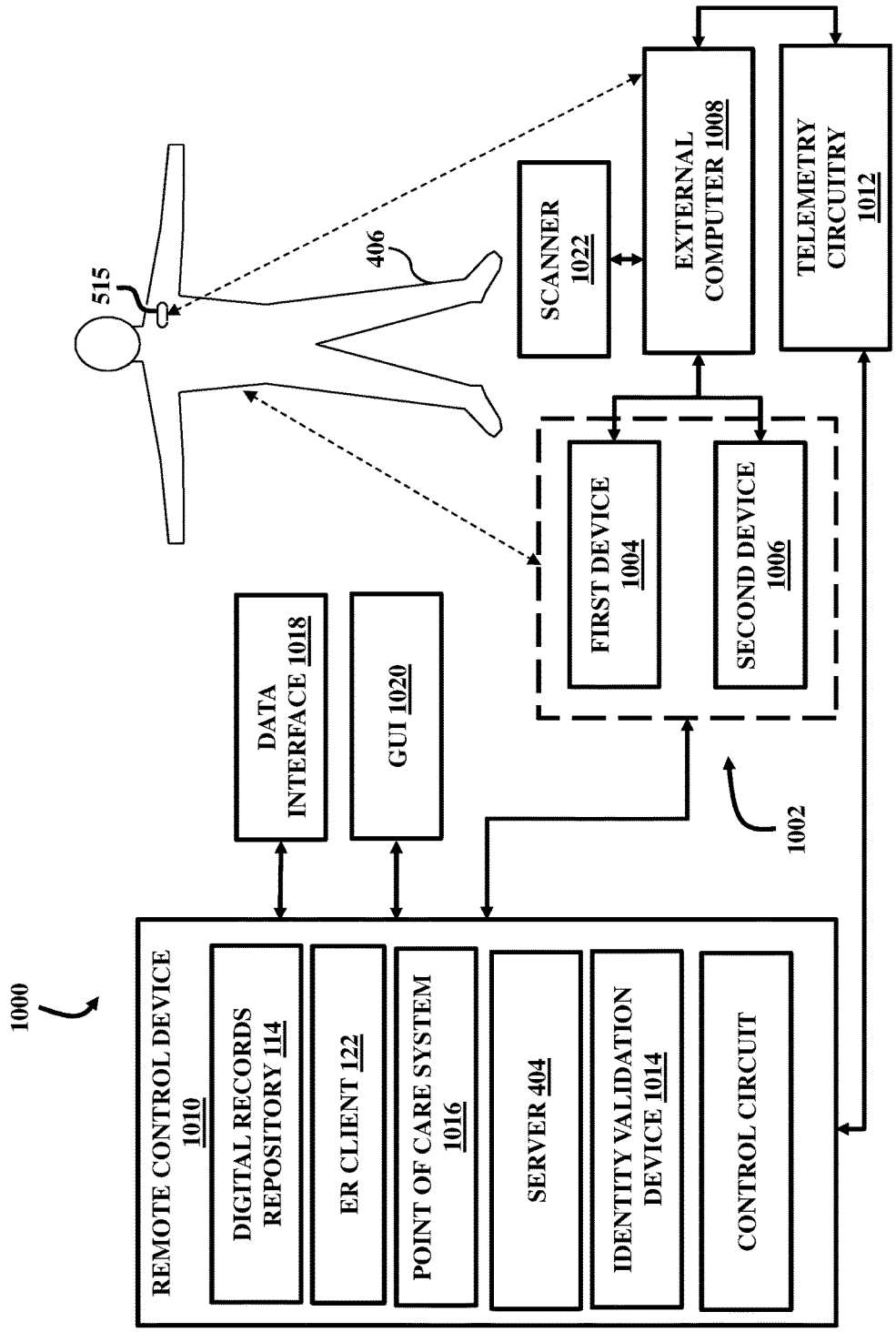
FIG. 10 illustrates an exemplary remote-control device in association with a multi-device module, in accordance with an embodiment.

FIG. 10 illustrates a distributed architecture-based system 1000 for a multi-device module 1002 in accordance with an embodiment. In the example herein, the multi-device module 1002 includes two devices, however, in other embodiments; more than two devices may be employed without limitations.

The distributed architecture-based system 1000 (hereafter referred to as system 1000) includes the physiological sensor 515 (also referred to as physiological sensor 515 elsewhere interchangeably without limitations) associated with a body of a subject. The physiological sensor 515 is configured to sense one or more physiological characteristics of the subject 406 and generate a digital physiological signal. The digital physiological signal is indicative of an instantaneous physiological state of the subject 406. The instantaneous physical state may represent momentary physical state of the subject 406 at a particular moment of time. The physical state may include such as heart rate, blood pressure, blood sugar level, pulse rate, cardiac rhythm, and the like that may be captured using a specific component of the physiological sensor 515 or using multiple physiological sensors for detecting each type of physiological signal. The instantaneous physical state may change at every moment and accordingly the physiological sensor 515 may intermittently or regularly sense the physiological characteristics of the subject 406 and generate the corresponding digital physiological signal(s). In an example, the physiological sensor 515 may be implanted within a patient's body subcutaneously to sense intrinsic physiological characteristics. In an example, the physiological sensor 515 is associated with the subject 406 as an external device.

The system 1000 includes a first device 1004 of the multi-device module 1002 configured for bi-directional wireless communication and positioned proximate to the subject 406. The first device 1004 may be a medical device and may include a memory circuit and a processor. The first device 1004 may be configured to generate a signal indicative of an operating state of the first device 1004. The operating state may be a performing state or a non-performing state of the first device 1004. The system 1000 may include a second device 1006 of the multi-device module 1002 which may also be configured for bi-directional wireless communication and may be positioned proximate to the subject 406. The second device 1006 may also include a memory circuit and a processor similar to that of the first device 1004. The second device 1006 is configured to generate a signal indicative of an operating state of the second device 1006. The operating state can be one of a performing state and a non-performing state of the second device 1006. In some examples, the first device 1004 and the second device 1006 are configured to perform one of a therapeutic, diagnostic, and a medication delivery task on the subject in accordance with instructions obtained from an external computing device 1008 or from the EMR system 108 or manually by an operator.

The system 1000 may include a remote-control device 1010 positioned apart from the physiological sensor 515, the first device 1004, and the second device 1006. In an example, the first device 1004, second device 1006, and the physiological sensor 515 may be connected with the computer 1008 such that the remote-control device 1010 is communicatively connected with the first device 1004, second device 1006, and the physiological sensor 515 through the computer 1008. The computer 1008 may be located at a remote location from the remote-control device 1010. The computer 1008 may include telemetry circuitry 1012 for communicating with the physiological sensor 515, the first device 1004, and the second device 1006.

The remote-control device 1010 may include the EMR system 108 as discussed above. The EMR system 108 may include the digital records repository 114 which may include a memory circuit and a processing unit for storing dynamically updating computer executable files aggregated from the plurality of changing private networks and social networks or any other digital data sources 124. The computer executable files may contain dynamically updating digitally recorded information (the digital data as discussed earlier). The dynamically updating digitally recorded information or simply digital data may store information about a set of attributes associated with the subject that may reflect subject's vital and/or health parameters among other things. These medical parameters may be associated with changing reference values associated with the subject 406. For example, one of the attributes may be subject's cardiac rhythm recorded by an ECG machine such that reference values ass identified in an ECG report may be defined along with the attribute. If the subject 406 or any associated entity repeats the ECG, new values may be associated with the attribute of the subject 406. These attributes and the associated reference values may change as new medical records of the subject 406 get added in the EMR system 108. The varying reference values of the subject 406 for the set of parameters are indicative of medical status of the subject 406 at a particular time. However, these reference values are subject to updating of the medical records from the digital data sources 124 or by the subject 406. The reference values associated with the attributes may in certain cases be different than the information aggregated in real-time from the physiological sensor 515 which may demand an immediate intervention as discussed hereafter.

The EMR system 108 may include the ER client 122. The EMR system 108 may include or be communicatively connected with the server machine 404 (also referred to as server simply) as discussed earlier. Among the various tasks the server machine 404 may perform, the server machine 404 may also be configured for communicating with the physiological sensor 515, the first device 1004, and the second device 1006 either directly or through the computer 1008 associated with the first device 1004, second device 1006, and the physiological sensor 515. In an example, the computer 1008 may send a request for service to the server machine 404 which may indicate a request for operation of any of the devices in association with the subject 406 for delivering a particular medical procedure, therapy, performing diagnosis, delivering medication, etc. The server machine 404 may be configured to receive the service request and also receive the physiological signal from the physiological sensor 515 either directly or through the computer 1008. The server machine 404 is configured for receiving the digital physiological signal indicative of the instantaneous physiological state of the subject 406 and sending programmable operational parameters to the first device 1004 and the second device 1006 in response to the request for service from the computer 1008 and based on the instantaneous physiological state. The operating parameters decide operating characteristics of the first device 1004 and operating characteristics of the second device 1006 such as whether the first device 1004 and/or the second device 1006 should execute certain tasks and for what duration and in which precedence and priority. The operating characteristics of the first device 1004 and the operating characteristics of the second device 1006 are interdependent through priority and interdependence relationships as discussed earlier.

The server machine 404 may also receive a signal from the computer 1008 or along with the physiological signal indicative of an identity of the subject 406, the first device 1004, and the second device 1006, in an embodiment. In an embodiment, the identity of the subject 406 can be defined from the service request and the identity of the associated medical devices can be determined from the EMR system 108 for the subject 406.

The system 1000 may include an identity validation device 1014 coupled to the server machine 404 to verify identity of the first device 1004 and the second device 1006 and associate a subject identifier uniquely representing the subject 406 with the first device 1004 and the second device 1006 based on information contained within the physiological signal or the service request such that the operating parameters are calculated based on one or more of the reference values associated with the subject 406 having the unique subject identifier as identified based on the physiological signal. In an example, the physiological sensor 515 is configured for the subject 406 such that the digital physiological signal contains the subject identifier along with an information indicative of the instantaneous physiological state of the subject 406. In an embodiment, the identity is known from the service request. In an embodiment, the computer 1008 may send the service request along with details of the sensed physiological signal and the associated medical devices and identity of the subject 406 such that the identity may be verified using certain identifiers such as the subject identifier associated with the request from the computer 1008.

The remote-control device 1010 may be configured to associate the subject identifier with the computer executable files stored in the digital records repository 114 to retrieve the reference values associated with the subject 406 and generate an output indicative of the operational parameters of the first device 1004 and the second device 1006 based on the physiological signal and the retrieved reference values associated with the subject 406. The reference values may indicate health state and medical procedures of the subject 406 and the medical devices 1004 and 1006 associated with the subject 406 and operational guidelines for the medical devices 1004 and 1006 in association with the subject 406 such that the remote-control device 1010 can accordingly guide the medical devices 1004 and 1006 for the operations based on the medical records contained in the computer executable files for the subject 406.

The operational parameters may include one or more of changing an operating state of the first device 1004 only for a first period of time, changing an operating state of the second device 1006 only for a second period of time, changing an operating state of both the first device 1004 and the second device 1006 for a third period of time, and connecting a third device different from the first device 1004 and the second device 1006 by associating an operating state with the third device in association with the subject 406 for a fourth period of time. Each of the first device 1004, the second device 1006, and the third device are uniquely identified by device identifiers such that the digital records repository 114 stores the digital identifiers in the device manager 412 or a memory in association with the subject identifier. The switch matrix 510 may be configured to cause switching of the operating state of the one or more of the first device 1004, second device 1006, and the third device upon receipt of the operational parameters from the remote-control device 1010 in accordance with the priority and interdependence relationships. The remote-control device 1010 may include the time detection circuit 506 configured to monitor the first period of time, second period of time, third period of time, and the fourth period of time. The remote-control device 1010 may include the device state detection circuit 508 coupled to the time detection circuit 506 and configured to identify an operating state of the first device 1004, second device 1006, and the third device after completion of the first period of time, second period of time, third period of time, and the fourth period of time. The remote-control device 1010 may include the fault detection circuit 514 configured to generate a signal indicative of a fault if the device state detection circuit 508 does not detect a change in operating states of either of the first device 1004, second device 1006 or the third device in accordance with the operational parameters transmitted by the remote-control device 1010.

The EMR system 108 may also include a mobile point of care system 1016 to capture subject-associated digital data at a point of care. The point of care system 1016 may be defined as a location where the subject 406 is located or the subject 406 is cared in a hospital premise such that the mobile point of care system 1010 may be transported to various locations to capture the digital data associated with the subject 406. The point of care system 1016 is communicatively connected with the electronic record (ER) client 122 so as to transmit the electronic records or digital data captured by the mobile point of care system 1016 from the private networks 102 or from devices associated with the subject 406 to the server machine 404. The mobile point of care system 1016 may provide a data interface 1018 in communication with the mobile point of care system 1016 to facilitate transmission of the electronic records to the server machine 404. The point of care system 1016 may capture the digital records using bar codes, QR codes, data sharing techniques, or manual entries by the subject 406, Near Field communication techniques, and the like. The point of care system 1016 may include a subject data capture facility to enter information provided by a subject 406 or associated medical devices, a subject data repository, in communication with the point of care system 1016 and with external systems, to store the subject data for access by the point of care system 1016 and then transmit to the server machine 404 or the remote-control device 1010. In this way, the paint of care system 1016 may capture each piece of data at its source at the time of entry to provide a complete audit trail for all subject associated digital data.

The point of care system 1016 captures subject-associated data in real-time at the point of care, that is, where healthcare providers interact with their subjects or medical devices interact with the associated subjects. For example, physicians can use the point of care system 1016 to enter, access, process, analyze and annotate data from subject records in real-time at the point of care. Thus, using the point of care system 1016, a physician, who has many subjects in a hospital, can visit each subject in their room, access their electronic records there, enter results of current diagnosis, evaluate their medical history, electronically annotate their x-rays images and prescribe medications and treatments instantaneously as the point of care system 1016 captures and organizes subject-associated data into the medical records stored in the subject data repository. The point of care system 1016 may likewise communicate with a reference database to assist a healthcare provider in making diagnoses, prescribing medications and administering treatments.

The EMR system 108 may also configure a web-based interactive graphical user interface 1020 for alternatively allowing the subject 406 to enter the digital records manually from a distant location.

In an embodiment, one or more of the physiological sensor 515, the first device 1004, the second device 1006, and the computer 1008 are configured to transform the operating parameters into a digital data structure which may be readable by a scanner 1022. The digital data structure may be a QR (quick response) code.

Figure 11:
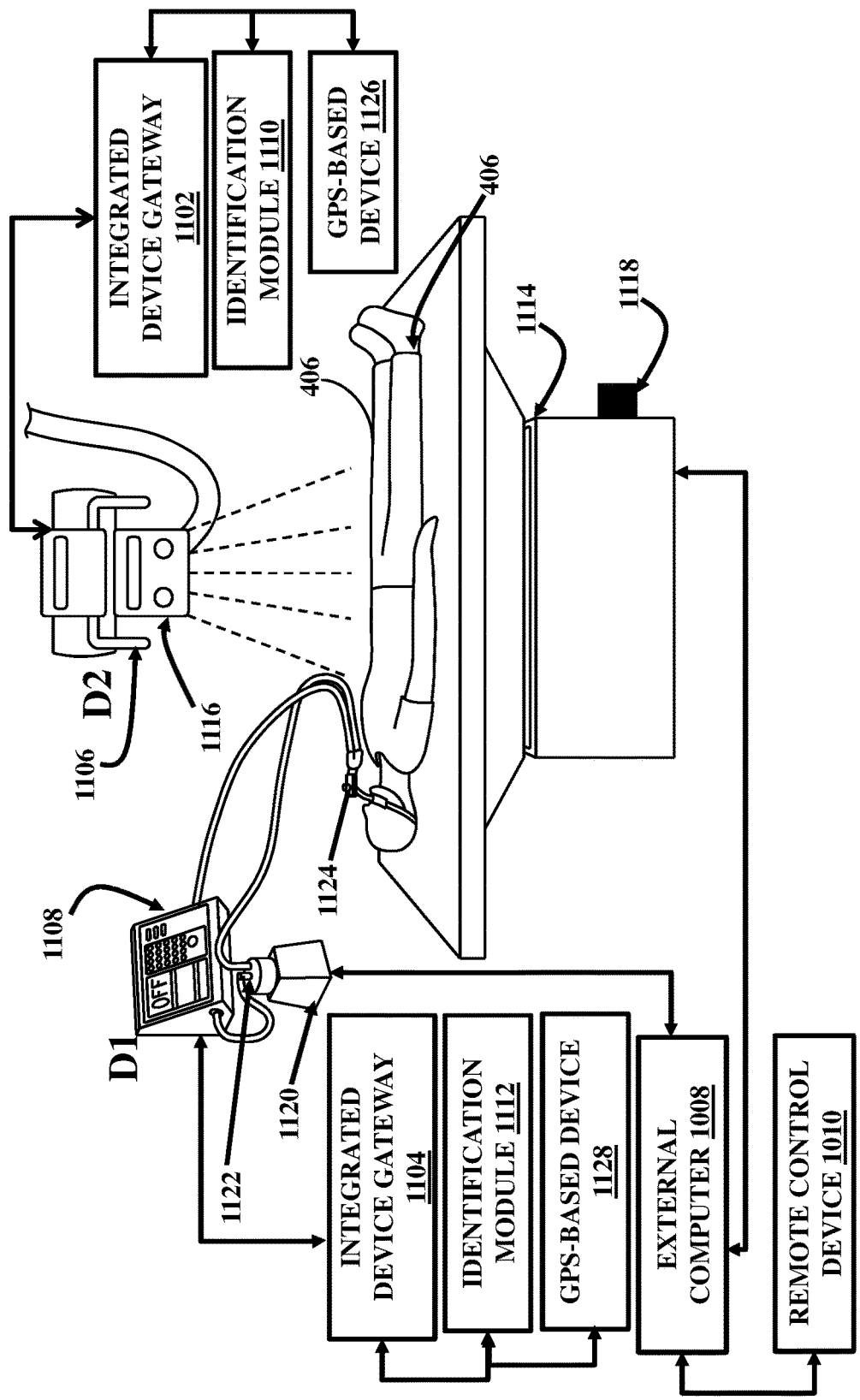
FIG. 11 illustrates an exemplary multi-device module, in accordance with an embodiment.

FIG. 11 illustrates the multi-device module 1002, in accordance with an embodiment herein. The multi-device module 1002 includes the first device 1004, the second device 1006, the computer 1008 configured for establishing an internet protocol connection with a dynamically interfaced device such as the EMR system 108 or the remote-control device 1010 via an internet protocol network interface for communicating with the dynamically interfaced device. In an example as shown in FIG. 11, the first device 1004 is a medical imaging device such as an X Ray machine and the second device 1006 is a life support system such as a ventilator such that the functioning of the medical imaging device 1004 is dependent on the functioning of the life support system 1006 such that the EMR system 108 controls the interdependence of the functioning of the medical imaging device 1004 and the life support system 1006 from a remote location through the computer 1008.

The first device 1004 includes an integrated device gateway 1102 configured to have a multiple interface unit comprising data interface units. The integrated device gateway 1102 is configured to send medical operation measurements which may represent operational details in conformity with the operational parameters received via a wired/wireless communication network from the remote-control device 1010 directly or through the computer 1008. The integrated device gateway 1102 can ensure, through recording of information and measurements and transmission to the computer 1008 and/or the remote-control device 1010, the operation of the first device 1004 is in accordance with the operational parameters received from the remote-control device 1010. Similarly, the second device 1006 can also include a similar integrate device gateway 1104 which measures performance of the second device 1006. Various accessories and circuitries of the first device 1004 and the second device 1006 are contained within respective housings 1106 and 1108 of the first device 1004 and the second device 1006.

Each of the first device 1004 and the second device 1006 may contain one or more of a therapeutic device, a medication delivery device, and a diagnosis device physically contained within the respective device housing 1106 and 1108 and configured to perform one of a therapeutic, diagnostic, and a medication delivery task depending on the nature of the first device 1004 and the second device 1006.

In an embodiment, the first device 1004 and the second device 1006 can respectively contain a first identification module 1110 and a second identification module 1112 to respectively contain digitally stored information indicative of device identifier and configured to be transmitted to other devices such as the remote-control device 1010 and the computer 1008 upon request for device identification. The computer 1008 may include the telemetry circuitry 1012 which allows communication with the physiological sensor 515 and the first device 1004, and the second device 1006. The computer 1008 may be configured to receive the physiological signal from the associated physiological sensor 515 configured for the subject 406. The computer 1008 may be configured to transmit a subject identifier, a first medical device identifier associated with the first medical device 1004, and a second medical device identifier associated with the second medical device 1006 along with the service request to the remote-control device 1010 located apart. The remote-control device 1010 is configured to fulfill the service request based on information contained in the plurality of dynamically updating computer executable files obtained from the plurality of digital data sources 124 and stored in the EMR system 108. The computer 1008 is further configured to receive the operational parameters from the remote-control device 1010 in response to the service request from the computer 1008 and based on the instantaneous physiological state as identified from the physiological signal such that the one or more operating parameters decides operating characteristics of the first medical device 1004 and operating characteristics of the second medical device 1006 as discussed earlier in the document.

As shown in the exemplary illustration, the first device 1004 is the medical imaging machine for imaging of a target such as a tissue or a bone structure within a body of the subject 406. The imaging machine includes a rotatable drive shaft 1114 made of a rigid material and configured to rotate along multiple axes. The medical imaging machine includes an imaging device 1116 supported on the rotatable drive shaft 1114. The imaging device 1116 is adapted to transmit energy toward the target such as in the form of X rays or magnetic energy. The medical imaging device includes a position adjustment mechanism 1118 coupling with the rotatable shaft 1114 to allow adjustment of the rotatable drive shaft 1114 in order to focus transmission of the energy at the target by aligning along the multiple axes.

The second device 1006 is the life support system. The life support system includes an oxygen source 1120 that includes a tank of pressurized gas. The life support system further includes one or more control valve 1122 disposed over a channel connecting the oxygen source 1120 and the subject 406 to allow the oxygen to flow from the tank/source 1120 to a laryngeal mask 1124 in a first state and to allow gas expelled from the subject 406 to flow from the laryngeal mask 1124 to the atmosphere in a second state while preventing the oxygen from flowing from the oxygen source 1120 in a second state. The life support system includes the laryngeal mask 1124 disposed downstream from the one or more control valve 1122. The laryngeal mask 1124 may be configured to form an air seal with the subject's respiratory tract such that the oxygen flows from the oxygen source 1120 to the lungs of the subject 406. The life support system may include a timer (not shown) for synchronizing actuation of the one or more control valve 1122 based on the operational parameters received from the remote-control device 1010.

The oxygen source 1120 may contain pressurized oxygen which may be supplied as per requirements by controlling supply from such as a supply regulator and a pressure gauge (not shown). The oxygen source 1120 stores substantially pure oxygen under pressure. The pressure of oxygen within the oxygen source drops during use because gas is supplied to the subject but not returned to the oxygen source. In one aspect, a medical-grade compressed-oxygen cylinder is used. In an example, the life support system is a ventilator.

In accordance with embodiments, a device such as the first device 1004 and second device 1006 may be provided or used for a particular subject such as 406. In an example, if the subject 406 is associated with the particular device, and when the EMR system 108 or the computer 1008 is used proximate to the device, the remote-control device 1010 automatically begins functioning in the context of the particular subject 406. In an embodiment, software can also be used to automatically connect to the subject 406 simply based on the device that the subject 406 is connected or associated with. In an embodiment, each of the first medical device 1004 and the second medical device 1006 may include respective (Global Positioning System) GPS-based devices 1126 and 1128 such that the GPS-based devices 1126 and 1128 are configured to detect geo-locations of the respective first medical device 1004 and the second medical device 1006. The remote-control device 1010 receives the detected geo-locations of the first medical device 1004 and the second medical device 1006, and the remote-control device 1010 automatically correlates the subject identifier for the subject 406 associated with the first medical device 1004 and the second medical device 1006 and initiates functioning in context of the subject 406 as and when the EMR system 108 or the computer 1008 is proximate to the subject 406 associated with the first medical device 1004 and the second medical device 1006.

Figure 12:
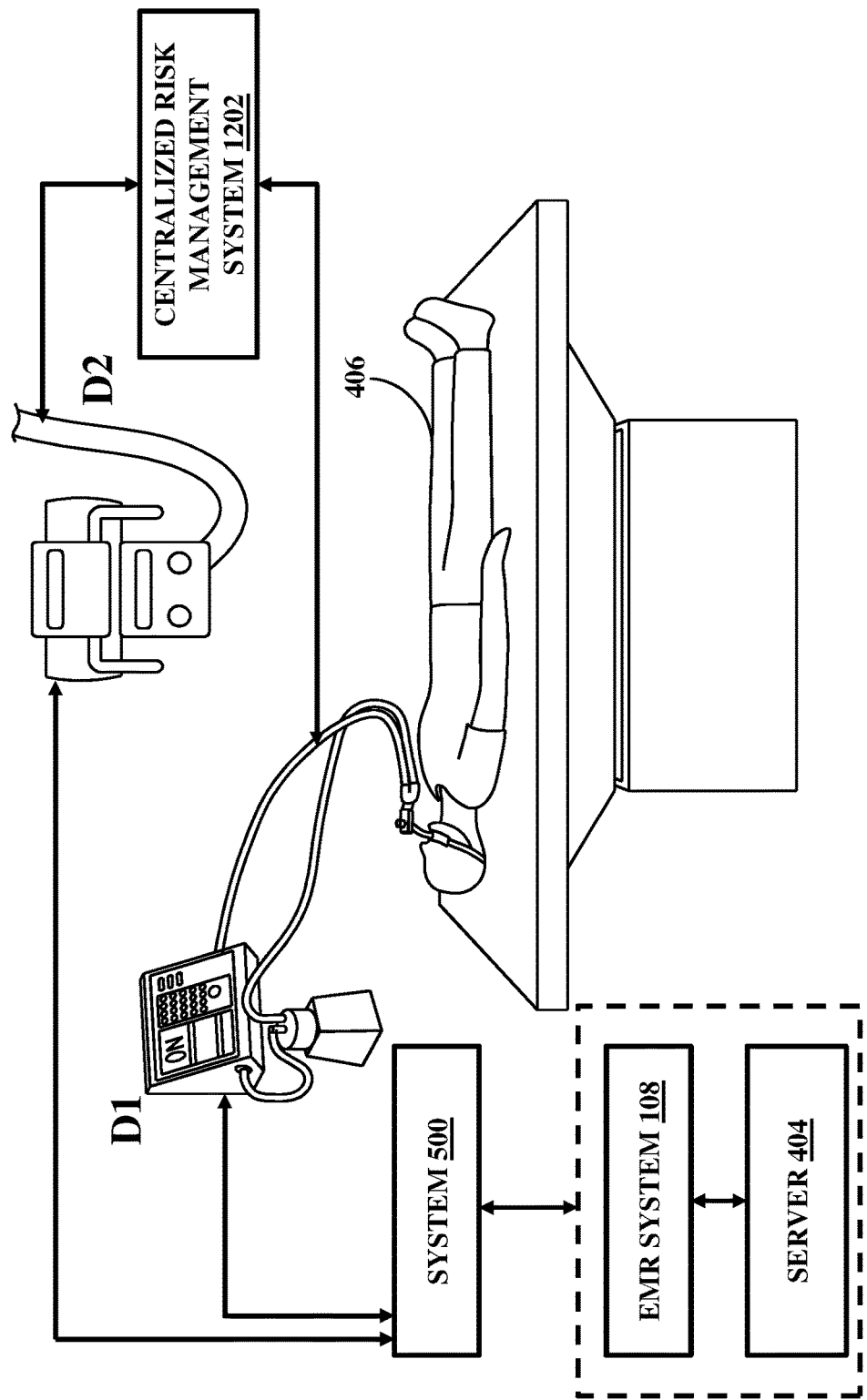
FIG. 12 illustrates an exemplary centralized system linked with medical devices, in accordance with an embodiment.

FIG. 12 illustrates an example wherein a centralized management system is coupled operatively and/or communicatively with the medical devices 1004 and 1006. The medical devices 1004 and 1006 may be assessed by the centralized management system for any vulnerability, safety or security related aspect before the medical devices 1004 and 1006 are connected with the system 500 and the EMR 108 or server 404 so as to ensure that only reliable medical devices communicate with the system 500 or server 404. In an embodiment, the computer 1008 may include the centralized management system 1202. In an embodiment, the centralized management system 1202 may not be integrated within the computer 1008, instead, it may be enabled by an external third party system communicatively connected with the computer 1008 and/or the medical devices 1004 and 1006.

The centralized management system 1202 may be configured to protect the network 104 from any potential threat or vulnerability. In an embodiment, the centralized management system 1202 may store a list of software and/or hardware assets that may be integrated within the medical devices 1004 and 1006 in a repository. Each of these assets may be vulnerable to particular threats. The centralized management system 1202 may also store associated potential vulnerabilities for each of the assets and also create a mapping between the assets and respective potential vulnerabilities. The centralized management system 1202 may also associate a rank to each vulnerability and asset combination which may be indicative of overall effect on the network 104 and ultimately allowing the centralized management system 1202 to make a decision whether the medical devices 1004 and 1006 are trustworthy enough to be integrated within the network 106 or not. The centralized management system 1202 may continuously monitor the vulnerabilities and the assets from a plurality of information sources and keep updating nature of association between the assets and the vulnerability now and then. The centralized management system 1202 may inform the system 500 and/or server 404 in case of any anomaly detection. The centralized management system 1202 may also reject a medical device from the network 106 in case of any anomaly detection. The centralized management system 1202 is configured to build security and compliance monitoring strategies that adapt to changing threats and regulatory requirements for the medical devices 1004 and 1006. The centralized management system 1202 may comprise a plurality of security systems and safety systems to monitor for the vulnerabilities and risks associated with the assets integrated within the medical devices 1004 and 1006. In an embodiment, the centralized management system 1202 may not be tied to the EMR 108 and may be deployed separately and may be configured to influence the medical devices 1004 and 1006 independently.

In embodiments, the centralized management system 1202 may include or connected to a risk information source receiving risk information, and generating a risk assessment report based on the risk information. The centralized management system 1202 may include or connected to an asset information source, and an analysis system that correlates one or more risks with one or more assets. In various embodiments, the centralized management system 1202 may generate a risk assessment report from the correlated risk information and asset information. The centralized management system 1202 may assess for risks globally that occur in any region or country throughout the world, for any type of risk or any type of asset.

The embodiments herein are discussed above with respect to the medical devices 1004 and 1006 located along with the subject in a hospital or any other medical premise which is connected communicatively with the EMR 108 and the server 108. In some embodiments, however the medical devices 1004 and 1006 may be located at certain other premises such as at home of a subject wherein the medical devices 1004 and 1006 may be used to monitor certain parameters of the patient and/or perform certain tasks based on monitored parameters by sensing devices around the subject such as the physiological sensor 515 as discussed earlier.

In accordance with certain embodiments, the devices may or may not be medical devices, and may include sensors or wearables or any other intelligent devices that may be located around an entity such as the subject or anyone else to sense the contextual parameters. These devices may be controlled by the EMR to perform certain tasks based on the monitored contextual parameters around the subject. For example, a sensor may be deployed to monitor humidity levels around the subject and as soon as the humidity levels reach a particular level, the device (a humidifier) may be informed to operate in accordance with custom rules coming from EMR in association with subject-specific information so as the humidity to be managed at the desired level for a particular subject in accordance with medical or comfort needs.

In an example, the embodiments herein can provide a computer program product configured to include a pre-configured set of instructions, which when performed, can result in actions as stated in conjunction with the method(s) described above. In an example, the pre-configured set of instructions can be stored on a tangible non-transitory computer readable medium. In an example, the tangible non-transitory computer readable medium can be configured to include the set of instructions, which when performed by a device, can cause the device to perform acts similar to the ones described here.

The embodiments herein may comprise a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments herein is depicted in FIG. 13, with reference to FIGS. 1 through 12. This schematic drawing illustrates a hardware configuration of an information handling/computer system 1300 in accordance with an exemplary embodiment herein. The system 1300 comprises at least one processor or central controller (CPU) 1310. The CPUs 1310 are interconnected via system bus 1312 to various devices such as a random access memory (RAM) 1314, read-only memory (ROM) 1316, and an input/output (I/O) adapter 1318. The I/O adapter 1318 can connect to peripheral devices, such as disk units 1311 and storage drives 1313, or other program storage devices that are readable by the system. The system 1300 can read the inventive instructions on the program storage devices and follow these instructions to execute the methodology of the embodiments herein. The system 1300 further includes a user interface adapter 1319 that connects a keyboard 1315, mouse 1317, speaker 1324, microphone 1322, and/or other user interface devices such as a touch screen device (not shown) to the bus 1312 to gather user input. Additionally, a communication adapter 1320 connects the bus 1312 to a data processing network 1325, and a display adapter 1321 connects the bus 1312 to a display device 1323, which provides a GUI (e.g., a gadget) in accordance with the embodiments herein, or which may be embodied as an output device such as a monitor, printer, or transmitter, for example. Further, a transceiver 1326, a signal comparator 1327, and a signal converter 1328 may be connected with the bus 1312 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for controlling multiple devices, said system comprising:
   a physiological sensor associated with a body of a subject and configured to sense one or more physiological characteristics of said subject and generate a digital physiological signal indicative of an instantaneous physiological state of said subject;
   a first device configured for bi-directional wireless communication positioned proximate to said subject and comprising a first memory circuit and a first processor, wherein said first device is configured to generate a first signal indicative of an operating state of said first device, and wherein said operating state comprising one of a performing state and a non-performing state of said first device;
   a second device configured for bi-directional wireless communication positioned proximate to said subject and comprising a second memory circuit and a second processor, wherein said second device is configured to generate a second signal indicative of an operating state of said second device, wherein said operating state comprising one of a performing state and a non-performing state of said second device, and wherein said first device and said second device are configured to perform one of a therapeutic, diagnostic, and a medication delivery task on said subject in accordance with computer-enabled instructions;
   a computer with telemetry circuitry for communicating with said physiological sensor, said first device, and said second device; and
   a remote-control device positioned apart from said physiological sensor, said first device, and said second device, wherein said remote-control device comprising:
      a digital records repository comprising a memory circuit and a processing unit for storing dynamically updating computer executable files aggregated from a plurality of changing private networks wherein said computer executable files contain dynamically updating digitally recorded information indicative of a set of changing subject attributes and respective changing reference values associated with said subject;
      an electronic record (ER) client configured to make a wireless connection with each of said private networks and configured to query an ER database associated with each of said private networks for electronic records residing within said private networks;
      a server machine configured for communicating with said physiological sensor, said first device, and said second device either directly or through said computer, wherein said server machine is configured for receiving said digital physiological signal indicative of said instantaneous physiological state of said subject and sending programmable operational parameters to said first device and said second device in response to a request for service from said computer and based on said instantaneous physiological state such that said operating parameters decides operating characteristics of said first device and operating characteristics of said second device and said operating characteristics of said first device and said operating characteristics of said second device are interdependent through a priority and interdependence relationship, wherein at least one of said physiological sensor, said first device, said second device, and said computer transforms said received operating parameters into a digital data structure readable by a scanner; and
      an identity validation device to verify an identity of said first device and said second device and associate a subject identifier uniquely representing said subject with said first device and said second device based on information contained within said physiological signal such that said operating parameters are calculated based on one or more of said reference values associated with said subject having said unique subject identifier as identified based on said physiological signal.

2. The system of claim 1, wherein said physiological sensor is implanted within said body of said subject subcutaneously.

3. The system of claim 1, wherein said physiological sensor is associated with said subject as an external device.

4. The system of claim 1, wherein said physiological sensor is configured for said subject such that said digital physiological signal contains said subject identifier along with an information indicative of said instantaneous physiological state of said subject.

5. The system of claim 4, wherein said remote-control device is configured to associate said subject identifier with said computer executable files stored in said digital records repository to retrieve said reference values associated with said subject and generate an output indicative of said operational parameters of said first device and said second device based on said physiological signal and said retrieved reference values associated with said subject.

6. The system of claim 5, wherein said operational parameters comprise any of:
   changing an operating state of said first device only for a first period of time;
   changing an operating state of said second device only for a second period of time;
   changing an operating state of both said first device and said second device for a third period of time; and
   connecting a third device different from said first device and said second device by associating an operating state with said third device in association with said subject for a fourth period of time,
   wherein each of said first device, said second device, and said third device are uniquely identified by device identifiers such that said digital records repository stores said digital identifiers in a device manager in association with said subject identifier.

7. The system of claim 6, wherein any of said server machine and said computer further comprise a switch matrix configured to cause switching of said operating state of said one or more of said first device, second device, and said third device upon receipt of said operational parameters from said remote-control device in accordance with said priority and interdependence relationships.

8. The system of claim 7, wherein said remote-control device further comprises a time detection circuit configured to monitor said first period of time, second period of time, third period of time, and said fourth period of time.

9. The system of claim 8, further comprising a device state detection circuit coupled to said time detection circuit and configured to identify an operating state of said first device, second device, and said third device after completion of said first period of time, said second period of time, said third period of time, and said fourth period of time.

10. The system of claim 9, further comprising a fault detection circuit configured to generate a signal indicative of a fault when said device state detection circuit does not detect a change in operating states of either of said first device, second device, or said third device in accordance with said operational parameters transmitted by said remote-control device.

11. The system of claim 1, wherein said first device comprises a ventilator and said second device comprises an X-ray machine such that said remote-control device causes said ventilator to perform a first action upon receipt and said X-ray machine to perform a second action upon receipt of said operational parameters.

12. The system of claim 1, wherein said remote-control device comprises an electronic medical record (EMR) system configured to house a plurality of digital records associated with a plurality of subjects including said subject in the form of a plurality of digital files including said computer executable files associated with said subject, wherein said EMR system comprising:
 said digital records repository;
 said electronic record (ER) client;
 a mobile point of care system to capture subject-associated digital data at a point of care wherein said point of care system is communicatively connected with said electronic record (ER) client so as to transmit said electronic records captured by said mobile point of care system from said private networks to said server machine;
 a data interface, in communication with said mobile point of care system, to facilitate transmission of said electronic records to said server machine; and
 a web-based interactive graphical user interface for allowing said subject to enter said digital records manually from a distant location.

13. The system of claim 1, wherein said digital data structure comprises a QR (quick response) code.

14. A multi-device system comprising:
 a first medical device configured for bi-directional wireless communication positioned proximate to a subject and comprising a first memory circuit and a first processor, wherein said first medical device is configured to generate a first signal indicative of an operating state of said first medical device, and wherein said operating state comprising one of a performing state and a non-performing state of said first medical device; and
 a second medical device configured for bi-directional wireless communication positioned proximate to said subject and comprising a second memory circuit and a second processor, wherein said second medical device is configured to generate a second signal indicative of an operating state of said second medical device, and wherein said operating state comprising one of a performing state and a non-performing state of said second medical device,
 wherein each of said first medical device and said second medical device comprising:
  an integrated gateway device configured to have a multiple interface unit comprising data interface units configured to send medical operation measurements in conformity with one or more operational parameters received via any of a wired and wireless communication network;
  a medical device housing to contain device accessories and circuitry;
  one or more of a therapeutic delivery device, a medication delivery device, and a diagnosis device physically contained within said medical device housing and configured to perform one of a therapeutic, diagnostic, and a medication delivery task;
  an identification module to contain digitally stored information indicative of device identifier and configured to be transmitted to other devices upon request for device identification; and
  a computer with telemetry circuitry for communicating with a physiological sensor, said first device, and said second device, wherein said computer configured to:
   receive a physiological signal from said associated physiological sensor configured for a subject;
   transmit a subject identifier, a first medical device identifier associated with said first medical device, and a second medical device identifier associated with said second medical device along with a service request to a remote-control device positioned apart from said physiological sensor, and wherein said remote-control device is configured to fulfill said service request based on information contained in a plurality of dynamically updating computer executable files from a plurality of digital data sources and stored in an EMR system configured within said remote-control device; and
   receive said one or more operational parameters from said remote-control device in response to a service request from said computer and based on an instantaneous physiological state as identified from said physiological signal such that said one or more operating parameters decides operating characteristics of said first medical device and operating characteristics of said second medical device, wherein said operating characteristics of said first medical device and said operating characteristics of said second medical device are interdependent through a priority and interdependence relationship.

15. The system of claim 14, wherein said first medical device comprises a medical imaging machine for imaging of a target including a tissue or a bone structure within a body of a subject, said medical imaging machine comprising:
 a rotatable drive shaft;
 an imaging device supported on said rotatable drive shaft, said imaging device adapted to transmit energy toward said target;
 a position adjustment mechanism coupling with said rotatable shaft to allow adjustment of said rotatable drive shaft in order to focus transmission of said energy at said target;
 said integrated gateway device; and
 said identification module.

16. The system of claim 15, wherein said energy comprises X-rays and said imaging machine comprises an X-Ray machine.

17. The system of claim 14, wherein said second medical device comprises a life support system comprising:
- an oxygen source that includes a tank of pressurized gas;
- one or more control valves disposed over a channel connecting said oxygen source and said subject to allow said oxygen to flow from said tank to a laryngeal mask in a first state and to allow gas expelled from said subject to flow from said laryngeal mask to said atmosphere in a second state while preventing said oxygen from flowing from said oxygen source in a second state;
- said laryngeal mask disposed downstream from said inspiration control valve, said laryngeal mask configured to form an air seal with said subject's respiratory tract such that said oxygen flows from said oxygen source to said lungs of said subject;
- a timer for synchronizing actuation of said one or more control valves based on said operational parameters received from said remote-control device containing said EMR system;
- said integrated gateway device; and
- said identification module.

18. The system of claim 17, wherein said life support system comprises a ventilator.

19. The system of claim 14, wherein each of said first medical device and said second medical device comprising a respective (Global Positioning System) GPS-based device such that said GPS-based device is configured to detect geo-locations of said respective first medical device and said second medical device, wherein said remote-control device receives said detected geo-locations of said first medical device and said second medical device, and said remote-control device automatically correlates said subject identifier for said subject associated with said first medical device and said second medical device and initiates functioning in context of said subject as and when said EMR system is proximate to said subject associated with said first medical device and said second medical device.

20. The system of claim 14, wherein said computer is configured to transform said operating parameters received from said remote-control device into a digital data structure, said system further comprising a scanner communicatively coupled to said computer such that said digital data structure is readable by said scanner.

* * * * *